US011098124B2

(12) United States Patent
Bay et al.

(10) Patent No.: US 11,098,124 B2
(45) Date of Patent: Aug. 24, 2021

(54) CD31$^{shed}$ AS A MOLECULAR TARGET FOR IMAGING OF INFLAMMATION

(71) Applicants: INSTITUT NATIONAL DE LA SANTE ET DE LA RECHERCHE MEDICALE (INSERM), Paris (FR); UNIVERSITÉ PARIS DIDEROT—PARIS 7, Paris (FR); UNIVERSITE PARIS 13—PARIS NORD, Villetaneuse (FR); ASSISTANCE PUBLIQUE—HOPITAUX DE PARIS, Paris (FR); INSTITUT PASTEUR, Paris (FR); CENTRE NATIONAL DE LA RECHERCHE SCIENTIFIQUE (CNRS), Paris (FR)

(72) Inventors: Sylvie Bay, Paris (FR); Antonino Nicoletti, Paris (FR); Dominique Le Guludec, Paris (FR); Jonathan Vigne, Paris (FR); Giuseppina Caligiuri, Paris (FR)

(73) Assignees: INSTITUT NATIONAL DE LA SANTE ET DE LA RECHERCHE MEDICALE (INSERM), Paris (FR); UNIVERSITE DE PARIS, Paris (FR); UNIVERSITE PARIS 13—PARIS NORD, Villentaneuse (FR); ASSISTANCE PUBLIQUE—HOPITAUX DE PARIS, Paris (FR); INSTITUT PASTEUR, Paris (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 0 days.

(21) Appl. No.: 16/098,488

(22) PCT Filed: May 3, 2017

(86) PCT No.: PCT/EP2017/060574
§ 371 (c)(1),
(2) Date: Nov. 2, 2018

(87) PCT Pub. No.: WO2019/191214
PCT Pub. Date: Nov. 9, 2017

(65) Prior Publication Data
US 2019/0092858 A1 Mar. 28, 2019

(30) Foreign Application Priority Data
May 3, 2016 (EP) .................... 16305516

(51) Int. Cl.
*A61K 51/08* (2006.01)
*C07K 7/06* (2006.01)
(Continued)

(52) U.S. Cl.
CPC ............ *C07K 16/283* (2013.01); *A61K 51/08* (2013.01); *A61K 51/088* (2013.01); *C07K 7/06* (2013.01);
(Continued)

(58) Field of Classification Search
CPC ............ A61K 2121/00; A61K 2123/00; A61K 51/00; A61K 51/08; A61K 51/088;
(Continued)

(56) References Cited

U.S. PATENT DOCUMENTS 8,951,743 B2 * 2/2015 Caligiuri .......... G01N 33/54313
435/7.2
9,127,086 B2 * 9/2015 Caligiuri ................. A61P 25/00
(Continued)

FOREIGN PATENT DOCUMENTS

WO 2010/000741 1/2010
WO 2010/000756 1/2010
(Continued)

OTHER PUBLICATIONS

Delbosc et al., "Porphyromonas gingivalis participates in pathogenesis of human abdominal aortic aneurysm by neutrophil activation. Proof of concept in rats," PLoS One. Apr. 13, 2011;6(4):e18679.
(Continued)

*Primary Examiner* — D. L. Jones
(74) *Attorney, Agent, or Firm* — Nixon & Vanderhye

(57) ABSTRACT

Disclosed is CD31$^{shed}$ for use as a molecular imaging target in the molecular imaging of an inflammatory condition. Administering the radiolabeled peptide P8RI as CD31$^{shed}$ ligand in different rat models of inflammation indeed showed that CD31$^{shed}$ is present on activated cells in a quantity allowing a detectable signal, whereas the noise signal corresponding to CD31$^{shed}$ present on activated circulating cells and on other organs or cells not involved in inflammation was little. Also disclosed is a labeled CD31$^{shed}$ ligand and the use thereof as a molecular imaging agent in the molecular imaging of an inflammatory condition. The molecular imaging of inflammatory sites particularly allows determining whether a subject suffers from or is at risk of having an inflammatory condition or is at risk of recurrence of an inflammatory condition after an anti-inflammatory treatment.

12 Claims, 4 Drawing Sheets
Specification includes a Sequence Listing.

(51) Int. Cl.
*C07K 16/28* (2006.01)
*G01N 33/60* (2006.01)

(52) U.S. Cl.
CPC .......... *G01N 33/60* (2013.01); *A01K 2227/10* (2013.01); *A01K 2267/0368* (2013.01); *A01K 2267/0393* (2013.01); *G01N 2333/70596* (2013.01); *G01N 2800/7095* (2013.01)

(58) Field of Classification Search
CPC ........ C07K 16/283; C07K 7/06; G01N 33/60; G01N 2800/7095; G01N 2333/70596; A01K 2267/0393; A01K 2267/0368; A01K 2227/10
USPC .......... 424/1.11, 1.49, 1.65, 1.69, 1.73, 1.81, 424/1.85, 1.89, 9.1, 9.2, 9.3, 9.4, 9.5, 9.6; 514/1, 1.1, 19.2, 19.3, 19.4, 19.5, 19.6; 534/7, 10–16; 530/300
See application file for complete search history.

(56) References Cited

U.S. PATENT DOCUMENTS

| | | | |
|---|---|---|---|
| 9,534,036 B2* | 1/2017 | Caligiuri | G01N 33/6872 |
| 9,977,030 B2* | 5/2018 | Caligiuri | G01N 33/54313 |
| 10,253,085 B2* | 4/2019 | Caligiuri | A61P 7/02 |
| 10,815,272 B2* | 10/2020 | Caligiuri | A61P 3/10 |
| 2011/0229981 A1* | 9/2011 | Caligiuri | G01N 33/54313 |
| | | | 436/501 |

FOREIGN PATENT DOCUMENTS

| | | |
|---|---|---|
| WO | 2013/152919 | 10/2013 |
| WO | 2013/190014 | 12/2013 |

OTHER PUBLICATIONS

Fornasa et al.,"TCR stimulation drives cleavage and shedding of the ITIM receptor CD31," J Immunol. May 15, 2010;184(10):5485-92.

Fornasa et al., "A CD31-derived peptide prevents angiotensin II-induced atherosclerosis progression and aneurysm formation," Cardiovascular Research Apr. 1, 2012;94(1):30-37.

International search report for PCT application PCT/EP2017/060574, dated Jul. 7, 2017.

Fang, W. et al., "Evaluation of 99mTc-labeled Cyclic RGD peptide with a PEG4 linker for thrombosis imaging: comparison with DMP444." Bioconjug Chem. Aug. 17, 2011;22(8):1715-22.

\* cited by examiner

A

B

SEQUENCE LISTING

```
<160> NUMBER OF SEQ ID NOS: 74

<210> SEQ ID NO 1
<211> LENGTH: 738
<212> TYPE: PRT
<213> ORGANISM: Homo sapiens
<220> FEATURE:
<221> NAME/KEY: SIGNAL
<222> LOCATION: (1)..(27)
<220> FEATURE:
<221> NAME/KEY: DOMAIN
<222> LOCATION: (28)..(601)
<223> OTHER INFORMATION: Extracellular domain
<220> FEATURE:
<221> NAME/KEY: DOMAIN
<222> LOCATION: (34)..(121)
<223> OTHER INFORMATION: First Ig-like domain
<220> FEATURE:
```

```
<221> NAME/KEY: DOMAIN
<222> LOCATION: (145)..(233)
<223> OTHER INFORMATION: Second Ig-like domain
<220> FEATURE:
<221> NAME/KEY: DOMAIN
<222> LOCATION: (236)..(315)
<223> OTHER INFORMATION: Third Ig-like domain
<220> FEATURE:
<221> NAME/KEY: DOMAIN
<222> LOCATION: (328)..(401)
<223> OTHER INFORMATION: Fourth Ig-like domain
<220> FEATURE:
<221> NAME/KEY: DOMAIN
<222> LOCATION: (424)..(493)
<223> OTHER INFORMATION: Fifth Ig-like domain
<220> FEATURE:
<221> NAME/KEY: DOMAIN
<222> LOCATION: (499)..(591)
<223> OTHER INFORMATION: Sixth Ig-like domain
<220> FEATURE:
<221> NAME/KEY: DOMAIN
<222> LOCATION: (592)..(601)
<223> OTHER INFORMATION: Juxta-membrane domain
<220> FEATURE:
<221> NAME/KEY: DOMAIN
<222> LOCATION: (602)..(620)
<223> OTHER INFORMATION: Transmembrane domain
<220> FEATURE:
<221> NAME/KEY: DOMAIN
<222> LOCATION: (621)..(738)
<223> OTHER INFORMATION: Cytoplasmic domain

<400> SEQUENCE: 1
```

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Leu Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

-continued

```
Ser Pro Thr Gly Met Ile Met Glu Gly Ala Gln Leu His Ile Lys Cys
                245                 250                 255
Thr Ile Gln Val Thr His Leu Ala Gln Glu Phe Pro Glu Ile Ile Ile
            260                 265                 270
Gln Lys Asp Lys Ala Ile Val Ala His Asn Arg His Gly Asn Lys Ala
        275                 280                 285
Val Tyr Ser Val Met Ala Met Val Glu His Ser Gly Asn Tyr Thr Cys
    290                 295                 300
Lys Val Glu Ser Ser Arg Ile Ser Lys Val Ser Ser Ile Val Val Asn
305                 310                 315                 320
Ile Thr Glu Leu Phe Ser Lys Pro Glu Leu Glu Ser Ser Phe Thr His
                325                 330                 335
Leu Asp Gln Gly Glu Arg Leu Asn Leu Ser Cys Ser Ile Pro Gly Ala
            340                 345                 350
Pro Pro Ala Asn Phe Thr Ile Gln Lys Glu Asp Thr Ile Val Ser Gln
        355                 360                 365
Thr Gln Asp Phe Thr Lys Ile Ala Ser Lys Ser Asp Ser Gly Thr Tyr
    370                 375                 380
Ile Cys Thr Ala Gly Ile Asp Lys Val Val Lys Lys Ser Asn Thr Val
385                 390                 395                 400
Gln Ile Val Val Cys Glu Met Leu Ser Gln Pro Arg Ile Ser Tyr Asp
                405                 410                 415
Ala Gln Phe Glu Val Ile Lys Gly Gln Thr Ile Glu Val Arg Cys Glu
            420                 425                 430
Ser Ile Ser Gly Thr Leu Pro Ile Ser Tyr Gln Leu Leu Lys Thr Ser
        435                 440                 445
Lys Val Leu Glu Asn Ser Thr Lys Asn Ser Asn Asp Pro Ala Val Phe
    450                 455                 460
Lys Asp Asn Pro Thr Glu Asp Val Glu Tyr Gln Cys Val Ala Asp Asn
465                 470                 475                 480
Cys His Ser His Ala Lys Met Leu Ser Glu Val Leu Arg Val Lys Val
                485                 490                 495
Ile Ala Pro Val Asp Glu Val Gln Ile Ser Ile Leu Ser Ser Lys Val
            500                 505                 510
Val Glu Ser Gly Glu Asp Ile Val Leu Gln Cys Ala Val Asn Glu Gly
        515                 520                 525
Ser Gly Pro Ile Thr Tyr Lys Phe Tyr Arg Glu Lys Glu Gly Lys Pro
    530                 535                 540
Phe Tyr Gln Met Thr Ser Asn Ala Thr Gln Ala Phe Trp Thr Lys Gln
545                 550                 555                 560
Lys Ala Ser Lys Glu Gln Glu Gly Glu Tyr Tyr Cys Thr Ala Phe Asn
                565                 570                 575
Arg Ala Asn His Ala Ser Ser Val Pro Arg Ser Lys Ile Leu Thr Val
            580                 585                 590
Arg Val Ile Leu Ala Pro Trp Lys Lys Gly Leu Ile Ala Val Val Ile
        595                 600                 605
Ile Gly Val Ile Ile Ala Leu Leu Ile Ile Ala Ala Lys Cys Tyr Phe
    610                 615                 620
Leu Arg Lys Ala Lys Ala Lys Gln Met Pro Val Glu Met Ser Arg Pro
625                 630                 635                 640
Ala Val Pro Leu Leu Asn Ser Asn Asn Glu Lys Met Ser Asp Pro Asn
                645                 650                 655
Met Glu Ala Asn Ser His Tyr Gly His Asn Asp Asp Val Arg Asn His
```

```
                    660                 665                 670
Ala Met Lys Pro Ile Asn Asp Asn Lys Glu Pro Leu Asn Ser Asp Val
                675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr

<210> SEQ ID NO 2
<211> LENGTH: 6
<212> TYPE: PRT
<213> ORGANISM: Artificial Sequence
<220> FEATURE:
<223> OTHER INFORMATION: muse or human-derived CD31 peptide

<400> SEQUENCE: 2

Leu Ala Pro Trp Lys Lys
1               5

<210> SEQ ID NO 3
<211> LENGTH: 10
<212> TYPE: PRT
<213> ORGANISM: Artificial Sequence
<220> FEATURE:
<223> OTHER INFORMATION: mouse-derived CD31 peptide

<400> SEQUENCE: 3

Val Arg Val Phe Leu Ala Pro Trp Lys Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: human-derived CD31 peptide

<400> SEQUENCE: 4

Val Arg Val Ile Leu Ala Pro Trp Lys Lys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: murine-derived CD31 peptide

<400> SEQUENCE: 5

Arg Val Phe Leu Ala Pro Trp Lys
1               5

<210> SEQ ID NO 6
<211> LENGTH: 8
<212> TYPE: PRT
<213> ORGANISM: Artificial Sequence
<220> FEATURE:
<223> OTHER INFORMATION: murine-derived CD31 peptide

<400> SEQUENCE: 6

Lys Trp Pro Ala Leu Phe Val Arg
```

-continued

<210> SEQ ID NO 7
<211> LENGTH: 8
<212> TYPE: PRT
<213> ORGANISM: Artificial Sequence
<220> FEATURE:
<223> OTHER INFORMATION: human-derived CD31 peptide

<400> SEQUENCE: 7

Arg Val Ile Leu Ala Pro Trp Lys
1               5

<210> SEQ ID NO 8
<211> LENGTH: 8
<212> TYPE: PRT
<213> ORGANISM: Artificial Sequence
<220> FEATURE:
<223> OTHER INFORMATION: human-derived CD31 sequence

<400> SEQUENCE: 8

Lys Trp Pro Ala Leu Ile Val Arg
1               5

<210> SEQ ID NO 9
<211> LENGTH: 727
<212> TYPE: PRT
<213> ORGANISM: Mus musculus

<400> SEQUENCE: 9

Met Leu Leu Ala Leu Gly Leu Thr Leu Val Leu Tyr Ala Ser Leu Gln
1               5                   10                  15

Ala Glu Glu Asn Ser Phe Thr Ile Asn Ser Ile His Met Glu Ser Leu
                20                  25                  30

Pro Ser Trp Glu Val Met Asn Gly Gln Gln Leu Thr Leu Glu Cys Leu
            35                  40                  45

Val Asp Ile Ser Thr Thr Ser Lys Ser Arg Ser Gln His Arg Val Leu
    50                  55                  60

Phe Tyr Lys Asp Asp Ala Met Val Tyr Asn Val Thr Ser Arg Glu His
65                  70                  75                  80

Thr Glu Ser Tyr Val Ile Pro Gln Ala Arg Val Phe His Ser Gly Lys
                85                  90                  95

Tyr Lys Cys Thr Val Met Leu Asn Asn Lys Glu Lys Thr Thr Ile Glu
                100                 105                 110

Tyr Glu Val Lys Val His Gly Val Ser Lys Pro Lys Val Thr Leu Asp
            115                 120                 125

Lys Lys Glu Val Thr Glu Gly Gly Val Val Thr Val Asn Cys Ser Leu
    130                 135                 140

Gln Glu Glu Lys Pro Pro Ile Phe Phe Lys Ile Glu Lys Leu Glu Val
145                 150                 155                 160

Gly Thr Lys Phe Val Lys Arg Arg Ile Asp Lys Thr Ser Asn Glu Asn
                165                 170                 175

Phe Val Leu Met Glu Phe Pro Ile Glu Ala Gln Asp His Val Leu Val
                180                 185                 190

Phe Arg Cys Gln Ala Gly Ile Leu Ser Gly Phe Lys Leu Gln Glu Ser
            195                 200                 205

Glu Pro Ile Arg Ser Glu Tyr Val Thr Val Gln Glu Ser Phe Ser Thr
    210                 215                 220

Pro Lys Phe Glu Ile Lys Pro Pro Gly Met Ile Ile Glu Gly Asp Gln

```
            225                 230                 235                 240
Leu His Ile Arg Cys Ile Val Gln Val Thr His Leu Val Gln Glu Phe
                245                 250                 255
Thr Glu Ile Ile Ile Gln Lys Asp Lys Ala Ile Val Ala Thr Ser Lys
                260                 265                 270
Gln Ser Ser Glu Ala Val Tyr Ser Val Met Ala Met Val Glu Tyr Ser
                275                 280                 285
Gly His Tyr Thr Cys Lys Val Glu Ser Asn Arg Ile Ser Lys Ala Ser
                290                 295                 300
Ser Ile Met Val Asn Ile Thr Glu Leu Phe Pro Lys Pro Lys Leu Glu
305                 310                 315                 320
Phe Ser Ser Arg Leu Asp Gln Gly Glu Leu Leu Asp Leu Ser Cys
                325                 330                 335
Ser Val Ser Gly Thr Pro Val Ala Asn Phe Thr Ile Gln Lys Glu Glu
                340                 345                 350
Thr Val Leu Ser Gln Tyr Gln Asn Phe Ser Lys Ile Ala Glu Glu Ser
                355                 360                 365
Asp Ser Gly Glu Tyr Ser Cys Thr Ala Gly Ile Gly Lys Val Val Lys
370                 375                 380
Arg Ser Gly Leu Val Pro Ile Gln Val Cys Glu Met Leu Ser Lys Pro
385                 390                 395                 400
Ser Ile Phe His Asp Ala Lys Ser Glu Ile Ile Lys Gly His Ala Ile
                405                 410                 415
Gly Ile Ser Cys Gln Ser Glu Asn Gly Thr Ala Pro Ile Thr Tyr His
                420                 425                 430
Leu Met Lys Ala Lys Ser Asp Phe Gln Thr Leu Glu Val Thr Ser Asn
                435                 440                 445
Asp Pro Ala Thr Phe Thr Asp Lys Pro Thr Arg Asp Met Glu Tyr Gln
                450                 455                 460
Cys Arg Ala Asp Asn Cys His Ser His Pro Ala Val Phe Ser Glu Ile
465                 470                 475                 480
Leu Arg Val Arg Val Ile Ala Pro Val Asp Glu Val Val Ile Ser Ile
                485                 490                 495
Leu Ser Ser Asn Glu Val Gln Ser Gly Ser Glu Met Val Leu Arg Cys
                500                 505                 510
Ser Val Lys Glu Gly Thr Ser Pro Ile Thr Phe Gln Phe Tyr Lys Glu
                515                 520                 525
Lys Glu Asp Arg Pro Phe His Gln Ala Val Val Asn Asp Thr Gln Ala
                530                 535                 540
Phe Trp His Asn Lys Gln Ala Ser Lys Lys Gln Glu Gly Gln Tyr Tyr
545                 550                 555                 560
Cys Thr Ala Ser Asn Arg Ala Ser Ser Met Arg Thr Ser Pro Arg Ser
                565                 570                 575
Ser Thr Leu Ala Val Arg Val Phe Leu Ala Pro Trp Lys Lys Gly Leu
                580                 585                 590
Ile Ala Val Val Val Ile Gly Val Val Ile Ala Thr Leu Ile Val Ala
                595                 600                 605
Ala Lys Cys Tyr Phe Leu Arg Lys Ala Lys Ala Lys Gln Lys Pro Val
                610                 615                 620
Glu Met Ser Arg Pro Ala Ala Pro Leu Leu Asn Ser Asn Ser Glu Lys
625                 630                 635                 640
Ile Ser Glu Pro Ser Val Glu Ala Asn Ser His Tyr Gly Tyr Asp Asp
                645                 650                 655
```

```
Val Ser Gly Asn Asp Ala Val Lys Pro Ile Asn Gln Asn Lys Asp Pro
            660                 665                 670

Gln Asn Met Asp Val Glu Tyr Thr Glu Val Glu Val Ser Ser Leu Glu
            675                 680                 685

Pro His Gln Ala Leu Gly Thr Arg Ala Thr Glu Thr Val Tyr Ser Glu
            690                 695                 700

Ile Arg Lys Val Asp Pro Asn Leu Met Glu Asn Arg Tyr Ser Arg Thr
705                 710                 715                 720

Glu Gly Ser Leu Asn Gly Thr
                725

<210> SEQ ID NO 10
<211> LENGTH: 739
<212> TYPE: PRT
<213> ORGANISM: Bos taurus

<400> SEQUENCE: 10

Met Gln Leu Arg Trp Thr Gln Arg Gly Met Met Trp Leu Gly Ala Leu
1               5                   10                  15

Leu Thr Leu Leu Leu Cys Ser Ser Leu Lys Gly Gln Glu Asn Ser Phe
            20                  25                  30

Thr Ile Asn Ser Ile His Met Gln Ile Leu Pro His Ser Thr Val Gln
            35                  40                  45

Asn Gly Glu Asn Leu Thr Leu Gln Cys Leu Val Asp Val Ser Thr Thr
        50                  55                  60

Ser Arg Val Lys Pro Leu His Gln Val Leu Phe Tyr Lys Asp Asp Val
65                  70                  75                  80

Leu Leu His Asn Val Ser Ser Arg Arg Asn Thr Glu Ser Tyr Leu Ile
                85                  90                  95

Pro His Val Arg Val Cys Asp Ser Gly Arg Tyr Lys Cys Asn Val Ile
            100                 105                 110

Leu Asn Asn Lys Glu Lys Thr Thr Pro Glu Tyr Glu Val Trp Val Lys
        115                 120                 125

Gly Val Ser Asp Pro Arg Val Thr Leu Asp Lys Lys Glu Val Ile Glu
    130                 135                 140

Gly Gly Val Val Val Asn Cys Ser Val Pro Glu Glu Lys Ala Pro
145                 150                 155                 160

Val His Phe Thr Ile Glu Lys Phe Glu Leu Asn Ile Arg Gly Ala Lys
                165                 170                 175

Lys Lys Arg Glu Lys Thr Ser Gln Asn Gln Asn Phe Val Thr Leu Glu
            180                 185                 190

Phe Thr Val Glu Glu Gln Asp Arg Thr Ile Arg Phe Gln Cys Gln Ala
        195                 200                 205

Lys Ile Phe Ser Gly Ser Asn Val Glu Ser Ser Arg Pro Ile Gln Ser
    210                 215                 220

Asp Leu Val Thr Val Arg Glu Ser Phe Ser Asn Pro Lys Phe His Ile
225                 230                 235                 240

Ile Pro Glu Gly Lys Val Met Glu Gly Asp Leu Gln Val Lys Cys
                245                 250                 255

Thr Val Gln Val Thr His Gln Ala Gln Ser Phe Pro Glu Ile Ile Ile
            260                 265                 270

Gln Lys Asp Arg Glu Ile Val Ala His Asn Ser Leu Ser Ser Glu Ala
        275                 280                 285

Val Tyr Ser Val Met Ala Thr Thr Glu His Asn Gly Asn Tyr Thr Cys
```

```
                290                 295                 300
Lys Val Glu Ala Ser Arg Ile Ser Lys Val Ser Ser Val Val Asn
305                 310                 315                 320

Val Thr Glu Leu Phe Ser Lys Pro Lys Leu Glu Ser Ser Ala Thr His
            325                 330                 335

Leu Asp Gln Gly Glu Asp Leu Asn Leu Leu Cys Ser Ile Pro Gly Ala
                340                 345                 350

Pro Pro Ala Asn Phe Thr Ile Gln Lys Gly Gly Met Thr Val Ser Gln
            355                 360                 365

Thr Gln Asn Phe Thr Lys Arg Val Ser Glu Trp Asp Ser Gly Leu Tyr
        370                 375                 380

Thr Cys Val Ala Gly Val Gly Arg Val Phe Lys Arg Ser Asn Thr Val
385                 390                 395                 400

Gln Ile Thr Val Cys Glu Met Leu Ser Lys Pro Ser Ile Phe His Asp
                405                 410                 415

Ser Arg Ser Glu Val Ile Lys Gly Gln Thr Ile Glu Val Ser Cys Gln
            420                 425                 430

Ser Val Asn Gly Thr Ala Pro Ile Phe Tyr Gln Leu Ser Asn Thr Ser
        435                 440                 445

Lys Pro Val Ala Asn Gln Ser Val Gly Ser Asn Lys Pro Ala Ile Phe
    450                 455                 460

Arg Val Lys Pro Thr Lys Asp Val Glu Tyr Cys Cys Ser Ala Asp Asn
465                 470                 475                 480

Cys His Ser His Ser Lys Met Phe Ser Glu Val Leu Arg Val Lys Val
                485                 490                 495

Ile Ala Pro Val Asp Glu Ala Gln Leu Val Val Leu Lys Gly Glu Val
            500                 505                 510

Glu Pro Gly Glu Pro Ile Val Phe Tyr Cys Ser Val Asn Glu Gly Ser
        515                 520                 525

Phe Pro Ile Thr Tyr Lys Phe Tyr Lys Glu Lys Glu Ser Lys Pro Phe
    530                 535                 540

Tyr Gln Asp Thr Ile Asn Ala Thr Gln Ile Met Trp His Lys Thr Thr
545                 550                 555                 560

Ala Ser Lys Glu Tyr Glu Gly Gln Tyr Tyr Cys Thr Ala Ser Asn Arg
                565                 570                 575

Ala Asn Leu Ser Lys His Val Ile Gln Ser Asn Thr Leu Thr Val Arg
            580                 585                 590

Val Tyr Leu Pro Leu Glu Lys Gly Leu Ile Ala Val Val Ile Gly
        595                 600                 605

Val Ile Ile Val Thr Leu Val Leu Gly Ala Lys Cys Tyr Phe Leu Lys
610                 615                 620

Lys Ala Lys Ala Lys Gln Met Pro Val Glu Met Ser Arg Pro Ala Val
625                 630                 635                 640

Pro Leu Leu Asn Ser Asn Asn Glu Lys Thr Leu Ser Asp Ala Gly Thr
            645                 650                 655

Glu Ala Asp Arg His Tyr Gly Tyr Asn Glu Asp Val Gly Asn His Ala
        660                 665                 670

Met Lys Pro Leu Asn Glu Asn Lys Glu Pro Leu Thr Leu Asp Val Glu
    675                 680                 685

Tyr Thr Glu Val Glu Val Thr Ser Pro Glu Pro His Gln Gly Leu Gly
690                 695                 700

Thr Lys Gly Thr Glu Thr Glu Val Tyr Ser Glu Ile Arg Lys Ala
705                 710                 715                 720
```

Asp Pro Asp Phe Val Glu Asn Arg Tyr Ser Arg Thr Glu Gly Ser Leu
                725                 730                 735

Asp Gly Ser

<210> SEQ ID NO 11
<211> LENGTH: 740
<212> TYPE: PRT
<213> ORGANISM: Sus scrofa

<400> SEQUENCE: 11

Met Arg Leu Arg Trp Thr Gln Gly Gly Asn Met Trp Leu Gly Val Leu
1               5                   10                  15

Leu Thr Leu Gln Leu Cys Ser Ser Leu Glu Gly Gln Glu Asn Ser Phe
            20                  25                  30

Thr Ile Asn Ser Ile His Met Glu Met Leu Pro Gly Gln Glu Val His
        35                  40                  45

Asn Gly Glu Asn Leu Thr Leu Gln Cys Ile Val Asp Val Ser Thr Thr
    50                  55                  60

Ser Ser Val Lys Pro Gln His Gln Val Leu Phe Tyr Lys Asp Asp Val
65                  70                  75                  80

Leu Phe His Asn Val Ser Ser Thr Lys Asn Thr Glu Ser Tyr Phe Ile
                85                  90                  95

Ser Glu Ala Arg Val Tyr Asn Ser Gly Arg Tyr Lys Cys Thr Val Ile
            100                 105                 110

Leu Asn Asn Lys Glu Lys Thr Thr Ala Glu Tyr Lys Val Val Val Glu
        115                 120                 125

Gly Val Ser Asn Pro Arg Val Thr Leu Asp Lys Lys Glu Val Ile Glu
    130                 135                 140

Gly Gly Val Val Lys Val Thr Cys Ser Val Pro Glu Glu Lys Pro Pro
145                 150                 155                 160

Val His Phe Ile Ile Glu Lys Phe Glu Leu Asn Val Arg Asp Val Lys
                165                 170                 175

Gln Arg Arg Glu Lys Thr Ala Asn Asn Gln Asn Ser Val Thr Leu Glu
            180                 185                 190

Phe Thr Val Glu Glu Gln Asp Arg Val Ile Leu Phe Ser Cys Gln Ala
        195                 200                 205

Asn Val Ile Phe Gly Thr Arg Val Glu Ile Ser Asp Ser Val Arg Ser
    210                 215                 220

Asp Leu Val Thr Val Arg Glu Ser Phe Ser Asn Pro Lys Phe His Ile
225                 230                 235                 240

Ser Pro Lys Gly Val Ile Ile Glu Gly Asp Gln Leu Leu Ile Lys Cys
                245                 250                 255

Thr Ile Gln Val Thr His Gln Ala Gln Ser Phe Pro Glu Ile Ile Ile
            260                 265                 270

Gln Lys Asp Lys Glu Ile Val Ala His Ser Arg Asn Gly Ser Glu Ala
        275                 280                 285

Val Tyr Ser Val Met Ala Thr Val Glu His Asn Ser Asn Tyr Thr Cys
    290                 295                 300

Lys Val Glu Ala Ser Arg Ile Ser Lys Val Ser Ser Ile Met Val Asn
305                 310                 315                 320

Ile Thr Glu Leu Phe Ser Arg Pro Lys Leu Lys Ser Ser Ala Thr Arg
                325                 330                 335

Leu Asp Gln Gly Glu Ser Leu Arg Leu Trp Cys Ser Ile Pro Gly Ala
            340                 345                 350

```
Pro Pro Glu Ala Asn Phe Thr Ile Gln Lys Gly Gly Met Met Met Leu
    355                 360                 365

Gln Asp Gln Asn Leu Thr Lys Val Ala Ser Glu Arg Asp Ser Gly Thr
370                 375                 380

Tyr Thr Cys Val Ala Gly Ile Gly Lys Val Val Lys Arg Ser Asn Glu
385                 390                 395                 400

Val Gln Ile Ala Val Cys Glu Met Leu Ser Lys Pro Ser Ile Phe His
                405                 410                 415

Asp Ser Gly Ser Glu Val Ile Lys Gly Gln Thr Ile Glu Val Ser Cys
            420                 425                 430

Gln Ser Ile Asn Gly Thr Ser Pro Ile Ser Tyr Gln Leu Leu Lys Gly
        435                 440                 445

Ser Asp Leu Leu Ala Ser Gln Asn Val Ser Ser Asn Glu Pro Ala Val
    450                 455                 460

Phe Lys Asp Asn Pro Thr Lys Asp Val Glu Tyr Gln Cys Ile Ala Asp
465                 470                 475                 480

Asn Cys His Ser His Ala Gly Met Pro Ser Lys Val Leu Arg Val Lys
                485                 490                 495

Val Ile Ala Pro Val Glu Val Lys Leu Ser Ile Leu Leu Ser Glu
            500                 505                 510

Glu Val Glu Ser Gly Gln Ala Ile Val Leu Gln Cys Ser Val Lys Glu
        515                 520                 525

Gly Ser Gly Pro Ile Thr Tyr Lys Phe Tyr Lys Glu Lys Glu Asn Lys
    530                 535                 540

Pro Phe His Gln Val Thr Leu Asn Asp Thr Gln Ala Ile Trp His Lys
545                 550                 555                 560

Pro Lys Ala Ser Lys Asp Gln Glu Gly Gln Tyr Tyr Cys Leu Ala Ser
                565                 570                 575

Asn Arg Ala Thr Pro Ser Lys Asn Phe Leu Gln Ser Asn Ile Leu Ala
            580                 585                 590

Val Arg Val Tyr Leu Ala Pro Trp Lys Lys Gly Leu Ile Ala Val Val
        595                 600                 605

Val Ile Ala Val Ile Ile Ala Val Leu Leu Gly Ala Arg Phe Tyr
    610                 615                 620

Phe Leu Lys Lys Ser Lys Ala Lys Gln Met Pro Val Glu Met Cys Arg
625                 630                 635                 640

Pro Ala Ala Pro Leu Leu Asn Ser Asn Asn Glu Lys Thr Leu Ser Asp
                645                 650                 655

Pro Asn Thr Glu Ala Asn Arg His Tyr Gly Tyr Asn Glu Asp Val Gly
            660                 665                 670

Asn His Ala Met Lys Pro Leu Asn Glu Asn Lys Glu Pro Leu Thr Leu
        675                 680                 685

Asp Val Glu Tyr Thr Glu Val Glu Val Thr Ser Pro Glu Pro His Arg
    690                 695                 700

Gly Leu Gly Thr Lys Gly Thr Glu Thr Val Tyr Ser Glu Ile Arg Lys
705                 710                 715                 720

Ala Asp Pro Asp Leu Val Glu Asn Arg Tyr Ser Arg Thr Glu Gly Ser
                725                 730                 735

Leu Asp Gly Thr
            740

<210> SEQ ID NO 12
<211> LENGTH: 23
```

```
<212> TYPE: PRT
<213> ORGANISM: Artificial Sequence
<220> FEATURE:
<223> OTHER INFORMATION: human-derived CD31 peptide

<400> SEQUENCE: 12

Asn His Ala Ser Ser Val Pro Arg Ser Lys Ile Leu Thr Val Arg Val
1               5                   10                  15

Ile Leu Ala Pro Trp Lys Lys
            20

<210> SEQ ID NO 13
<211> LENGTH: 15
<212> TYPE: PRT
<213> ORGANISM: Artificial Sequence
<220> FEATURE:
<223> OTHER INFORMATION: peptide

<400> SEQUENCE: 13

Ser Ser Thr Leu Ala Val Arg Val Phe Leu Ala Pro Trp Lys Lys
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: peptide

<400> SEQUENCE: 14

Ser Thr Leu Ala Val Arg Val Phe Leu Ala Pro Trp Lys Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide

<400> SEQUENCE: 15

Thr Leu Ala Val Arg Val Phe Leu Ala Pro Trp Lys Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: peptide

<400> SEQUENCE: 16

Leu Ala Val Arg Val Phe Leu Ala Pro Trp Lys Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: peptide

<400> SEQUENCE: 17

Ala Val Arg Val Phe Leu Ala Pro Trp Lys Lys
1               5                   10
```

```
<210> SEQ ID NO 18
<211> LENGTH: 9
<212> TYPE: PRT
<213> ORGANISM: Artificial Sequence
<220> FEATURE:
<223> OTHER INFORMATION: peptide

<400> SEQUENCE: 18

Arg Val Phe Leu Ala Pro Trp Lys Lys
1               5

<210> SEQ ID NO 19
<211> LENGTH: 8
<212> TYPE: PRT
<213> ORGANISM: Artificial Sequence
<220> FEATURE:
<223> OTHER INFORMATION: peptide

<400> SEQUENCE: 19

Val Phe Leu Ala Pro Trp Lys Lys
1               5

<210> SEQ ID NO 20
<211> LENGTH: 7
<212> TYPE: PRT
<213> ORGANISM: Artificial Sequence
<220> FEATURE:
<223> OTHER INFORMATION: peptide

<400> SEQUENCE: 20

Phe Leu Ala Pro Trp Lys Lys
1               5

<210> SEQ ID NO 21
<211> LENGTH: 5
<212> TYPE: PRT
<213> ORGANISM: Artificial Sequence
<220> FEATURE:
<223> OTHER INFORMATION: peptide

<400> SEQUENCE: 21

Ala Pro Trp Lys Lys
1               5

<210> SEQ ID NO 22
<211> LENGTH: 4
<212> TYPE: PRT
<213> ORGANISM: Artificial Sequence
<220> FEATURE:
<223> OTHER INFORMATION: peptide

<400> SEQUENCE: 22

Pro Trp Lys Lys
1

<210> SEQ ID NO 23
<211> LENGTH: 15
<212> TYPE: PRT
<213> ORGANISM: Artificial Sequence
<220> FEATURE:
<223> OTHER INFORMATION: peptide

<400> SEQUENCE: 23

Ser Lys Ile Leu Thr Val Arg Val Ile Leu Ala Pro Trp Lys Lys
1               5                   10                  15

<210> SEQ ID NO 24
```

```
<211> LENGTH: 14
<212> TYPE: PRT
<213> ORGANISM: Artificial Sequence
<220> FEATURE:
<223> OTHER INFORMATION: peptide

<400> SEQUENCE: 24

Lys Ile Leu Thr Val Arg Val Ile Leu Ala Pro Trp Lys Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: peptide

<400> SEQUENCE: 25

Ile Leu Thr Val Arg Val Ile Leu Ala Pro Trp Lys Lys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: peptide

<400> SEQUENCE: 26

Leu Thr Val Arg Val Ile Leu Ala Pro Trp Lys Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: peptide

<400> SEQUENCE: 27

Thr Val Arg Val Ile Leu Ala Pro Trp Lys Lys
1               5                   10

<210> SEQ ID NO 28
<211> LENGTH: 9
<212> TYPE: PRT
<213> ORGANISM: Artificial Sequence
<220> FEATURE:
<223> OTHER INFORMATION: peptide

<400> SEQUENCE: 28

Arg Val Ile Leu Ala Pro Trp Lys Lys
1               5

<210> SEQ ID NO 29
<211> LENGTH: 8
<212> TYPE: PRT
<213> ORGANISM: Artificial Sequence
<220> FEATURE:
<223> OTHER INFORMATION: peptide

<400> SEQUENCE: 29

Val Ile Leu Ala Pro Trp Lys Lys
1               5

<210> SEQ ID NO 30
<211> LENGTH: 7
```

<212> TYPE: PRT
<213> ORGANISM: Artificial Sequence
<220> FEATURE:
<223> OTHER INFORMATION: peptide

<400> SEQUENCE: 30

Ile Leu Ala Pro Trp Lys Lys
1               5

<210> SEQ ID NO 31
<211> LENGTH: 15
<212> TYPE: PRT
<213> ORGANISM: Artificial Sequence
<220> FEATURE:
<223> OTHER INFORMATION: peptide

<400> SEQUENCE: 31

Ser Ser Met Arg Thr Ser Pro Arg Ser Ser Thr Leu Ala Val Arg
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: peptide

<400> SEQUENCE: 32

Ser Ser Met Arg Thr Ser Pro Arg Ser Ser Thr Leu Ala Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: peptide

<400> SEQUENCE: 33

Ser Ser Met Arg Thr Ser Pro Arg Ser Ser Thr Leu Ala
1               5                   10

<210> SEQ ID NO 34
<211> LENGTH: 12
<212> TYPE: PRT
<213> ORGANISM: Artificial Sequence
<220> FEATURE:
<223> OTHER INFORMATION: peptide

<400> SEQUENCE: 34

Ser Ser Met Arg Thr Ser Pro Arg Ser Ser Thr Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: peptide

<400> SEQUENCE: 35

Ser Ser Met Arg Thr Ser Pro Arg Ser Ser Thr
1               5                   10

<210> SEQ ID NO 36
<211> LENGTH: 10
<212> TYPE: PRT

```
<213> ORGANISM: Artificial Sequence
<220> FEATURE:
<223> OTHER INFORMATION: peptide

<400> SEQUENCE: 36

Ser Ser Met Arg Thr Ser Pro Arg Ser Ser
1               5                   10

<210> SEQ ID NO 37
<211> LENGTH: 9
<212> TYPE: PRT
<213> ORGANISM: Artificial Sequence
<220> FEATURE:
<223> OTHER INFORMATION: peptide

<400> SEQUENCE: 37

Ser Ser Met Arg Thr Ser Pro Arg Ser
1               5

<210> SEQ ID NO 38
<211> LENGTH: 8
<212> TYPE: PRT
<213> ORGANISM: Artificial Sequence
<220> FEATURE:
<223> OTHER INFORMATION: peptide

<400> SEQUENCE: 38

Ser Ser Met Arg Thr Ser Pro Arg
1               5

<210> SEQ ID NO 39
<211> LENGTH: 7
<212> TYPE: PRT
<213> ORGANISM: Artificial Sequence
<220> FEATURE:
<223> OTHER INFORMATION: peptide

<400> SEQUENCE: 39

Ser Ser Met Arg Thr Ser Pro
1               5

<210> SEQ ID NO 40
<211> LENGTH: 6
<212> TYPE: PRT
<213> ORGANISM: Artificial Sequence
<220> FEATURE:
<223> OTHER INFORMATION: peptide

<400> SEQUENCE: 40

Ser Ser Met Arg Thr Ser
1               5

<210> SEQ ID NO 41
<211> LENGTH: 5
<212> TYPE: PRT
<213> ORGANISM: Artificial Sequence
<220> FEATURE:
<223> OTHER INFORMATION: peptide

<400> SEQUENCE: 41

Ser Ser Met Arg Thr
1               5

<210> SEQ ID NO 42
<211> LENGTH: 4
<212> TYPE: PRT
<213> ORGANISM: Artificial Sequence
```

```
<220> FEATURE:
<223> OTHER INFORMATION: peptide

<400> SEQUENCE: 42

Ser Ser Met Arg
1

<210> SEQ ID NO 43
<211> LENGTH: 15
<212> TYPE: PRT
<213> ORGANISM: Artificial Sequence
<220> FEATURE:
<223> OTHER INFORMATION: peptide

<400> SEQUENCE: 43

Asn His Ala Ser Ser Val Pro Arg Ser Lys Ile Leu Thr Val Arg
1               5                   10                  15

<210> SEQ ID NO 44
<211> LENGTH: 14
<212> TYPE: PRT
<213> ORGANISM: Artificial Sequence
<220> FEATURE:
<223> OTHER INFORMATION: peptide

<400> SEQUENCE: 44

Asn His Ala Ser Ser Val Pro Arg Ser Lys Ile Leu Thr Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: peptide

<400> SEQUENCE: 45

Asn His Ala Ser Ser Val Pro Arg Ser Lys Ile Leu Thr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: peptide

<400> SEQUENCE: 46

Asn His Ala Ser Ser Val Pro Arg Ser Lys Ile Leu
1               5                   10

<210> SEQ ID NO 47
<211> LENGTH: 11
<212> TYPE: PRT
<213> ORGANISM: Artificial Sequence
<220> FEATURE:
<223> OTHER INFORMATION: peptide

<400> SEQUENCE: 47

Asn His Ala Ser Ser Val Pro Arg Ser Lys Ile
1               5                   10

<210> SEQ ID NO 48
<211> LENGTH: 10
<212> TYPE: PRT
<213> ORGANISM: Artificial Sequence
<220> FEATURE:
```

<223> OTHER INFORMATION: peptide

<400> SEQUENCE: 48

Asn His Ala Ser Ser Val Pro Arg Ser Lys
1               5                   10

<210> SEQ ID NO 49
<211> LENGTH: 9
<212> TYPE: PRT
<213> ORGANISM: Artificial Sequence
<220> FEATURE:
<223> OTHER INFORMATION: peptide

<400> SEQUENCE: 49

Asn His Ala Ser Ser Val Pro Arg Ser
1               5

<210> SEQ ID NO 50
<211> LENGTH: 8
<212> TYPE: PRT
<213> ORGANISM: Artificial Sequence
<220> FEATURE:
<223> OTHER INFORMATION: peptide

<400> SEQUENCE: 50

Asn His Ala Ser Ser Val Pro Arg
1               5

<210> SEQ ID NO 51
<211> LENGTH: 7
<212> TYPE: PRT
<213> ORGANISM: Artificial Sequence
<220> FEATURE:
<223> OTHER INFORMATION: peptide

<400> SEQUENCE: 51

Asn His Ala Ser Ser Val Pro
1               5

<210> SEQ ID NO 52
<211> LENGTH: 6
<212> TYPE: PRT
<213> ORGANISM: Artificial Sequence
<220> FEATURE:
<223> OTHER INFORMATION: peptide

<400> SEQUENCE: 52

Asn His Ala Ser Ser Val
1               5

<210> SEQ ID NO 53
<211> LENGTH: 5
<212> TYPE: PRT
<213> ORGANISM: Artificial Sequence
<220> FEATURE:
<223> OTHER INFORMATION: peptide

<400> SEQUENCE: 53

Asn His Ala Ser Ser
1               5

<210> SEQ ID NO 54
<211> LENGTH: 4
<212> TYPE: PRT
<213> ORGANISM: Artificial Sequence
<220> FEATURE:
<223> OTHER INFORMATION: peptide

<400> SEQUENCE: 54

Asn His Ala Ser
1

<210> SEQ ID NO 55
<211> LENGTH: 15
<212> TYPE: PRT
<213> ORGANISM: Artificial Sequence
<220> FEATURE:
<223> OTHER INFORMATION: peptide

<400> SEQUENCE: 55

Thr Ser Pro Arg Ser Ser Thr Leu Ala Val Arg Val Phe Leu Ala
1               5                   10                  15

<210> SEQ ID NO 56
<211> LENGTH: 13
<212> TYPE: PRT
<213> ORGANISM: Artificial Sequence
<220> FEATURE:
<223> OTHER INFORMATION: peptide

<400> SEQUENCE: 56

Ser Pro Arg Ser Ser Thr Leu Ala Val Arg Val Phe Leu
1               5                   10

<210> SEQ ID NO 57
<211> LENGTH: 11
<212> TYPE: PRT
<213> ORGANISM: Artificial Sequence
<220> FEATURE:
<223> OTHER INFORMATION: peptide

<400> SEQUENCE: 57

Pro Arg Ser Ser Thr Leu Ala Val Arg Val Phe
1               5                   10

<210> SEQ ID NO 58
<211> LENGTH: 9
<212> TYPE: PRT
<213> ORGANISM: Artificial Sequence
<220> FEATURE:
<223> OTHER INFORMATION: peptide

<400> SEQUENCE: 58

Arg Ser Ser Thr Leu Ala Val Arg Val
1               5

<210> SEQ ID NO 59
<211> LENGTH: 7
<212> TYPE: PRT
<213> ORGANISM: Artificial Sequence
<220> FEATURE:
<223> OTHER INFORMATION: peptide

<400> SEQUENCE: 59

Ser Ser Thr Leu Ala Val Arg
1               5

<210> SEQ ID NO 60
<211> LENGTH: 5
<212> TYPE: PRT
<213> ORGANISM: Artificial Sequence
<220> FEATURE:
<223> OTHER INFORMATION: peptide

```
<400> SEQUENCE: 60

Ser Thr Leu Ala Val
1               5

<210> SEQ ID NO 61
<211> LENGTH: 15
<212> TYPE: PRT
<213> ORGANISM: Artificial Sequence
<220> FEATURE:
<223> OTHER INFORMATION: peptide

<400> SEQUENCE: 61

Ser Val Pro Arg Ser Lys Ile Leu Thr Val Arg Val Ile Leu Ala
1               5                   10                  15

<210> SEQ ID NO 62
<211> LENGTH: 13
<212> TYPE: PRT
<213> ORGANISM: Artificial Sequence
<220> FEATURE:
<223> OTHER INFORMATION: peptide

<400> SEQUENCE: 62

Val Pro Arg Ser Lys Ile Leu Thr Val Arg Val Ile Leu
1               5                   10

<210> SEQ ID NO 63
<211> LENGTH: 11
<212> TYPE: PRT
<213> ORGANISM: Artificial Sequence
<220> FEATURE:
<223> OTHER INFORMATION: peptide

<400> SEQUENCE: 63

Pro Arg Ser Lys Ile Leu Thr Val Arg Val Ile
1               5                   10

<210> SEQ ID NO 64
<211> LENGTH: 9
<212> TYPE: PRT
<213> ORGANISM: Artificial Sequence
<220> FEATURE:
<223> OTHER INFORMATION: peptide

<400> SEQUENCE: 64

Arg Ser Lys Ile Leu Thr Val Arg Val
1               5

<210> SEQ ID NO 65
<211> LENGTH: 7
<212> TYPE: PRT
<213> ORGANISM: Artificial Sequence
<220> FEATURE:
<223> OTHER INFORMATION: peptide

<400> SEQUENCE: 65

Ser Lys Ile Leu Thr Val Arg
1               5

<210> SEQ ID NO 66
<211> LENGTH: 5
<212> TYPE: PRT
<213> ORGANISM: Artificial Sequence
<220> FEATURE:
<223> OTHER INFORMATION: peptide

<400> SEQUENCE: 66
```

Lys Ile Leu Thr Val
1               5

<210> SEQ ID NO 67
<211> LENGTH: 4
<212> TYPE: PRT
<213> ORGANISM: Artificial Sequence
<220> FEATURE:
<223> OTHER INFORMATION: peptide

<400> SEQUENCE: 67

Arg Val Phe Leu
1

<210> SEQ ID NO 68
<211> LENGTH: 5
<212> TYPE: PRT
<213> ORGANISM: Artificial Sequence
<220> FEATURE:
<223> OTHER INFORMATION: peptide

<400> SEQUENCE: 68

Arg Val Phe Leu Ala
1               5

<210> SEQ ID NO 69
<211> LENGTH: 6
<212> TYPE: PRT
<213> ORGANISM: Artificial Sequence
<220> FEATURE:
<223> OTHER INFORMATION: peptide

<400> SEQUENCE: 69

Arg Val Phe Leu Ala Pro
1               5

<210> SEQ ID NO 70
<211> LENGTH: 7
<212> TYPE: PRT
<213> ORGANISM: Artificial Sequence
<220> FEATURE:
<223> OTHER INFORMATION: peptide

<400> SEQUENCE: 70

Arg Val Phe Leu Ala Pro Trp
1               5

<210> SEQ ID NO 71
<211> LENGTH: 4
<212> TYPE: PRT
<213> ORGANISM: Artificial Sequence
<220> FEATURE:
<223> OTHER INFORMATION: peptide

<400> SEQUENCE: 71

Arg Val Ile Leu
1

<210> SEQ ID NO 72
<211> LENGTH: 5
<212> TYPE: PRT
<213> ORGANISM: Artificial Sequence
<220> FEATURE:
<223> OTHER INFORMATION: peptide

<400> SEQUENCE: 72

```
Arg Val Ile Leu Ala
1               5

<210> SEQ ID NO 73
<211> LENGTH: 6
<212> TYPE: PRT
<213> ORGANISM: Artificial Sequence
<220> FEATURE:
<223> OTHER INFORMATION: peptide

<400> SEQUENCE: 73

Arg Val Ile Leu Ala Pro
1               5

<210> SEQ ID NO 74
<211> LENGTH: 7
<212> TYPE: PRT
<213> ORGANISM: Artificial Sequence
<220> FEATURE:
<223> OTHER INFORMATION: peptide

<400> SEQUENCE: 74

Arg Val Ile Leu Ala Pro Trp
1               5
```

CD31 $^{shed}$ AS A MOLECULAR TARGET FOR IMAGING OF INFLAMMATION

FIELD OF THE INVENTION

The present invention relates to the molecular imaging of inflammatory sites, in particular for determining whether a subject suffers or is at risk of having or developing an inflammatory condition and for monitoring the changes in the extent of an inflammatory condition after an anti-inflammatory treatment.

BACKGROUND

Imaging of inflammation sites would be a useful tool for the diagnosis of an inflammation condition. The high level of glucose metabolism in inflammation has prompted to the use of $^{18}$F-FDG (2-deoxy-2-$^{18}$F-fluoro-D-glucose) PET. $^{18}$F-FDG however suffers from poor specificity and its high physiologic uptake in the heart, lung and brain limits its use. More specific targets for imaging inflamed tissues are therefore needed.

CD31 is a transmembrane glycoprotein receptor constitutively expressed by leukocytes, platelets and endothelial cells. It consists of a single chain molecule comprising six Ig-like extracellular domains, a short transmembrane segment and a cytoplasmic tail comprising two important tyrosine-based motifs (around Y663 and Y686) that act as Immunoreceptor Tyrosine-based Inhibitory Motifs (ITIMs). The structure of CD31 is shown in the Table 1 below.

TABLE 1

Structure of CD31

| Domain | Position on SEQ ID NO: 1 |
| --- | --- |
| Signal peptide | 1 to 27 |
| Extracellular domain | 28 to 601 |
| First Ig-like extracellular domain | 34 to 121 |
| Second Ig-like extracellular domain | 145 to 233 |
| Third Ig-like extracellular domain | 236 to 315 |
| Fourth Ig-like extracellular domain | 328 to 401 |
| Fifth Ig-like extracellular domain | 424 to 493 |
| Sixth Ig-like extracellular domain | 499 to 591 |
| Juxta-membrane domain | 592 to 601 |
| Transmembrane domain | 602 to 620 |
| Cytoplasmic domain | 621 to 738 |

Due to its homophilic and inhibitory functions, CD31 exerts a crucial role in the homeostasis of the circulation. In pro-inflammatory conditions, the homophilic portion of the receptor is lost due to a cleavage and activated cells express a truncated form of CD31. WO2010/000756 indeed discloses that CD31 is shed on activated/memory T lymphocytes between the 5th and the 6th extracellular Ig-like domains whereas WO2013/152919 discloses that activated platelets also express a CD31 that is truncated between the 6$^{th}$ extracellular domain and the juxtamembrane sequence. Both types of shed extracellular sequences of CD31 (referred to as "soluble CD31") are then released into the circulation, where they are present together with a soluble splice variant of CD31, produced by healthy endothelial cells. The remaining small CD31 ectodomain which remains anchored to the membrane after shedding is referred to as "CD31$^{shed}$". WO2010/000756 and WO2013/152919 discloses a method for diagnosing a thrombotic or an autoimmune disorder based on the detection of said soluble CD31 in a biological sample of an individual.

WO2010/000741 discloses peptides corresponding to juxta-membrane amino acids of the ectodomain of CD31 that are able to rescue the physiological immunoregulatory function of CD31, by specifically targeting CD31$^{shed}$ on activated leukocytes and platelets. Such peptides are useful for the treatment of thrombotic or autoimmune disorders. WO2013/190014 further discloses specific peptides of 8 amino acids, within the membrane juxta-proximal part of extracellular CD31, which hold useful for the treatment of thrombotic or inflammatory disorders and display physic-chemical properties that are more suitable for drug development.

There is still a need to provide reliable solutions for the imaging and diagnostic of inflammatory conditions.

DESCRIPTION OF THE INVENTION

The Inventors have unexpectedly found that CD31$^{shed}$ itself can be used as a molecular target for the diagnosis of an inflammatory condition, in particular by allowing the molecular imaging of inflammatory sites. CD31$^{shed}$ was indeed surprisingly found to be present on activated cells in a quantity allowing to obtain a detectable signal when using a labeled CD31$^{shed}$ ligand, whereas the noise signal corresponding to CD31$^{shed}$ present on activated circulating cells and on other organs or cells not involved in inflammation was little, thereby leading to a good signal to noise ratio. They have indeed shown in vivo in an animal model of inflammation that administering to said animal a radiolabeled CD31$^{shed}$ ligand specific for CD31$^{shed}$ allows localizing the inflammation site, due to the specific binding of the radiolabeled CD31$^{shed}$ ligand to the activated cells expressing CD31$^{shed}$ and its subsequent concentration in the inflammation site, whereas the remaining radiolabeled CD31$^{shed}$ ligand is rapidly cleared from the body of the animal.

In this context, the Inventors used peptide P8RI of sequence SEQ ID NO: 6 consisting of D-enantiomer amino acids coupled to HYNIC (6-Hydrazinopyridine-3-carboxylic acid) via a PEG spacer and radiolabeled with 99mTc. Said radiolabeled CD31$^{shed}$ ligand was found stable both in vitro and in vivo and specific to CD31$^{shed}$, with very low binding to plasma proteins.

Therefore, labelled CD31$^{shed}$ ligands, in particular small peptides, able to specifically bind to CD31$^{shed}$ are useful as a tracer for molecular imaging of inflammation.

One object of the present invention is thus a labeled CD31$^{shed}$ ligand comprising a CD31$^{shed}$ ligand and at least one imaging label, preferably at least one radionuclide.

Said CD31$^{shed}$ ligand is preferably:
a) a peptide selected in the group consisting of:
  (i) a peptide consisting of a fragment of 3 to 15 amino acids of the sequence defined by amino acids 579 to 601 of sequence SEQ ID NO: 1,
  (ii) a peptide consisting of a fragment of 3 to 15 amino acids of a sequence corresponding to the amino acids 579 to 601 of sequence SEQ ID NO: 1 in a non-human mammalian CD31,
  (iii) a peptide of 3 to 15 amino acids consisting of a sequence at least 70% identical to the sequence of peptide (i),
  (iv) a peptide consisting of a retro-inverso sequence of peptide (i), (ii) or (iii), and
  (v) the peptide (i), (ii), (iii) or (iv) comprising at least one or at least one further chemical modification,
or
b) a peptidomimetic of peptide a).

The CD31$^{shed}$ ligand of (v) preferably comprises at least one amino acid in the D-enantiomer form.

The CD31$^{shed}$ ligand is preferably selected in the group consisting of a peptide of sequence SEQ ID NO: 2, a peptide of sequence SEQ ID NO: 3, a peptide of sequence SEQ ID NO: 4, a peptide of sequence SEQ ID NO: 5, a peptide of sequence SEQ ID NO: 6 consisting of D-enantiomer amino acids, a peptide of sequence SEQ ID NO: 7 and a peptide of sequence SEQ ID NO: 8 consisting of D-enantiomer amino acids.

A preferred CD31$^{shed}$ ligand is a peptide of sequence SEQ ID NO: 5, or a peptide of sequence SEQ ID NO: 6 consisting of D-enantiomer amino acids.

The radionuclide of the labeled CD31$^{shed}$ ligand is preferably detectable by molecular imaging technique(s), such as Positron Emission Tomography (PET), Single Photon Emission Computed Tomography (SPECT), an hybrid of SPECT and/or PET, or their combinations.

For example, the radionuclide is technetium-99m (99mTc or $^{99m}$Tc), gallium-67 ($^{67}$Ga), gallium-68 ($^{68}$Ga), yttrium-90 ($^{90}$Y), indium-111 ($^{111}$In), rhenium-186 ($^{186}$Re), fluorine-18 ($^{18}$F), copper-64 ($^{64}$Cu) or thallium-201 ($^{201}$Tl).

A preferred labeled CD31$^{shed}$ ligand comprises a peptide of sequence SEQ ID NO: 6 consisting of D-enantiomer amino acids as CD31$^{shed}$ ligand and 99mTc as radionuclide.

In one preferred embodiment, the CD31$^{shed}$ ligand is coupled with HYNIC (6-Hydrazinopyridine-3-carboxylic acid), optionally via at least one spacer.

Another object of the present invention relates to the labeled CD31$^{shed}$ ligand as defined above for use as a molecular imaging agent for imaging of inflammatory sites, in particular for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition. The present invention also relates to the use of the labeled CD31$^{shed}$ ligand as defined above as a molecular imaging agent, in particular for imaging inflammation sites.

Another object of the present invention relates to a method, preferably an in vitro method, for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition, wherein said method comprises:
detecting the presence of CD31$^{shed}$ on the surface of cells with a labeled CD31$^{shed}$ ligand as defined above in a biological sample obtained from the subject.

Another object of the present invention relates to CD31$^{shed}$ for use as a molecular imaging target for imaging of inflammatory sites, more particularly for determining whether a subject suffers from an inflammatory condition, is at risk of having an inflammatory condition, is at risk of recurrence of an inflammatory condition after an anti-inflammatory treatment or for monitoring the efficacy of a treatment of an inflammatory condition. The present invention also relates to the use of CD31$^{shed}$ for use as a molecular imaging target, in particular for imaging inflammation sites.

Inflammatory Condition

An inflammatory condition underlies a large number of diseases. For example, the immune system is often involved with inflammatory conditions, as demonstrated in both allergic reactions and some myopathies, with many immune system disorders resulting in abnormal inflammation.

As used throughout the present specification, the term "inflammatory condition" includes but is not limited to a chronic inflammatory condition, an immune disorder, an autoimmune disorder, an acute and chronic grant alloimmune conditions, an acute and chronic infectious-driven inflammatory condition, a non-immune disease with etiological origins in inflammatory processes or their combinations.

The chronic inflammatory condition is for example inflammatory bowel disease, psoriasis, atopic dermatitis, cerebral amyloid angiopathy an/or vasculitis.

An immune disorder is for example allergies and/or myopathy.

The autoimmune disorder is for example rheumatoid arthritis (RA), multiple sclerosis (MS), inflammatory bowel disease (IBD), systemic lupus erythematodes (SLE), Graves' disease and/or diabetes mellitus.

Acute and chronic alloimmune conditions are for example allograft rejection or graft versus host disease (GVHD).

Acute and chronic infectious-driven inflammatory conditions include the formation of septic granulomas (abscess) and/or septic shock.

The non-immune disease with etiological origins in inflammatory processes is for example cancer, thrombosis, ischaemic and/or ischemia-reperfusion organ damage (for example heart and/or brain infarction) arterial inflammatory condition (such as atherothrombosis, arterial dissection and/or unhealed/thromboses arterial aneurysm) and/or neurodegenerative disease.

The inflammatory condition is for example selected from the group consisting of rheumatoid arthritis, multiple sclerosis, allergies, myopathy, inflammatory bowel disease, psoriasis, atopic dermatitis, cerebral amyloid angiopathy, vasculitis, systemic lupus erythematosus, Graves' disease, diabetes mellitus, acute or chronic graft rejection, cancer, thrombosis, atherothrombosis, ischaemic heart and/or brain infarction, and/or neurodegenerative disease.

Subject for Imaging, to be Diagnosed and/or Treated

A "subject" in the context of the present invention is a human being or a non-human mammal.

The terms "human being", "individual" or "patient" are herein synonymous and may be used interchangeably.

Said human being may be of any sex, for example male or female and of any age, for example an infant, child, adolescent, adult, elderly people.

A non-human mammal is preferably a mouse, rat, cat, dog, rabbit, hamster, swine, sheep, horse or primate.

The subject may suffer from an inflammatory condition, be suspected to suffer from an inflammatory condition, be at risk of having an inflammatory condition or be at risk of recurrence of an inflammatory condition.

The expressions "at risk of having an inflammatory condition", "at risk of suffering from an inflammatory condition" and "at risks of developing an inflammatory condition" are herein synonymous.

"Risk" in the context of the present invention, relates to the probability that an event will occur over a specific time period, for example the conversion to an inflammatory condition.

Imaging of Inflammation

The expressions "imaging of inflammation sites" and "imaging of inflammation" are herein synonymous.

Imaging of inflammation sites allows to localize the inflamed tissues and/or inflamed organs in the body of a subject.

Imaging of inflammation sites presents many advantages.

For example, imaging of inflammation sites allows diagnosing an inflammation condition, confirming an inflammation condition, localizing the inflamed tissues or organs, monitoring the response to a treatment, for example to an anti-inflammatory treatment, monitoring the inflammatory side-effects of a treatment, predicting the risk of developing an inflammatory condition and/or determining the risk of recurrence of an inflammatory condition after an anti-inflammatory treatment.

Imaging of inflammation sites may thus be used for determining whether a subject suffers from an inflammatory condition, is at risk of having an inflammatory condition, is at risk of recurrence of an inflammatory condition after an anti-inflammatory treatment or for monitoring the efficacy of a treatment of an inflammatory condition.

A molecular imaging target and/or a molecular imaging agent are needed to carry out imaging of inflammation.

As used herein, the term "molecular imaging target" refers to a compound that can be detected by using molecular imaging techniques.

As used herein, the term "molecular imaging agent" refers to a compound that can be used to detect specific biological elements, in particular a molecular imaging target, by using molecular imaging techniques.

The molecular imaging agent is preferably an agent coupled to an imaging label, covalently or non-covalently.

In the context of the invention, the molecular imaging agent is used to detect $CD31^{shed}$ in vivo or in vitro, for example in a blood sample of a subject.

$CD31^{shed}$ for Use as a Molecular Imaging Target

The present invention thus relates to $CD31^{shed}$ for use as a molecular imaging target for imaging of inflammation sites.

The present invention also relates to the use of $CD31^{shed}$ as a molecular imaging target for imaging of inflammation sites.

The present invention particularly relates to $CD31^{shed}$ for use as a molecular imaging target in a method for imaging inflammation sites, particularly in vivo.

As used herein "$CD31^{shed}$" refers to the remaining small CD31 ectodomain which remains anchored to the membrane of endothelial cells, platelets or leukocytes, after shedding of the CD31 transmembrane glycoprotein receptor.

$CD31^{shed}$ on the surface of activated endothelial cells, platelets and leukocytes lacks at least the $1^{st}$ to $5^{th}$ extracellular Ig-like domains of CD31.

$CD31^{shed}$ on the surface of activated platelets and activated endothelial cells lacks the $1^{st}$ to $5^{th}$ extracellular Ig-like domains of CD31 and at least one part of the 6th extracellular Ig-like domain.

$CD31^{shed}$ on the surface of activated leukocytes lacks the $1^{st}$ to $5^{th}$ extracellular Ig-like domains, but comprises the 6th extracellular Ig-like domain.

The present invention also relates to $CD31^{shed}$ for use as defined above, in a method, preferably an in vivo method, for determining whether a subject suffers from an inflammatory condition, is at risk of having an inflammatory condition, is at risk of recurrence of an inflammatory condition after an anti-inflammatory treatment or for monitoring the efficacy of a treatment of an inflammatory condition.

The present invention also relates to $CD31^{shed}$ for use for determining whether a subject suffers from an inflammatory condition, is at risk of having an inflammatory condition, is at risk of recurrence of an inflammatory condition after an anti-inflammatory treatment or for monitoring the efficacy of a treatment of an inflammatory condition, in particular in vivo.

The expression "inflammatory condition" and "imaging of inflammation sites" are as defined above.

$CD31^{shed}$ Ligand

The term "$CD31^{shed}$ ligand" refers to any compound that is able to specifically bind with $CD31^{shed}$.

The specific binding of a compound to $CD31^{shed}$ present on a cell surface may be assessed by any method well-known by the skilled person.

For example, the specific binding may be measured by plasmon surface resonance, flow cytometry or beta-imager.

In a preferred embodiment, the binding of a compound to be tested to $CD31^{shed}$ present on a cell surface is assessed as follows: the compound to be tested, or an irrelevant analogue as negative control, is bound to a fluorescent probe (e.g. fluoresceine). The compound is incubated at consecutive dilutions (for example 1, 10, 100 μmop with CD31+ cells (for example from a cell line, such as Jurkat T cells, or primary cells, such as peripheral blood T cells), at a density of $10^6$ cells/ml in a saline buffer comprising Ca++ and Mg++(HBSS, culture medium). Parallel conditions are incubated in the presence of a cell activator (e.g. TCR cross-linking, such as 1 μg/ml anti-CD3e antibodies+20 μg/ml secondary F(ab')2 fragment if the cells are T lymphocytes). The reaction is stopped after 5 or 20 minutes by repeated washing steps with cold buffer. Cells are fixed with paraformaldehyde and washed again. Binding of the compound to be tested on individual cells is detected by the relative fluorescent signal using a flow cytometer. A greater signal for the specific compound as compared to the control and in the conditions comprising the cell activator as compared to resting cells indicates appropriate binding to $CD31^{shed}$.

Alternatively, the compound to be tested, or an irrelevant analogue as negative control, is tested for its binding to activated endothelial cells (for example primary cells from human blood vessels of immortalized cell lines). The cells are cultured on collagen type I thin layer to confluence. For the activation, the cells are incubated with 20 ng/ml Human recombinant TNFa for 30 minutes in culture medium. The reaction is stopped by rinsing the cells with cold saline buffer and the cells are fixed (for instance with a Zinc-fixative solution for 10 minutes at room temperature). After extensive rinsing in a saline buffer comprising, activated endothelial cells are labeled by the compound to be tested, or an irrelevant analogue as negative control, is bound to a fluorescent probe (e.g. fluoresceine) and counterstained by a plasma membrane dye (e g Cell Mask™) and a nuclear staining (eg Hoechst 33342). Binding of the compound to be tested on individual cells is detected by the relative fluorescent signal using a fluorescence microscope. A greater signal for the specific compound as compared to the control and in the conditions comprising the cell activator as compared to resting cells indicates appropriate binding to $CD31^{shed}$.

The $CD31^{shed}$ ligand may be a peptide, a peptidomimetic, a chemical compound, an antibody or an aptamer.

The term "antibody" is thus used to refer to any antibody-like molecule that has an antigen binding region, and this term includes antibody fragments that comprise an antigen binding domain such as Fab', Fab, F(ab')2, single domain antibodies (DABs or VHH), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art. In some embodiments, the antibody is a monoclonal antibody. In some embodiments, the antibody is non-internalizing. As used herein the term "non-internalizing antibody" refers to an antibody, respectively, that has the property of to bind to a target antigen present on a cell surface, and that, when bound to its target antigen, does not enter the cell and become degraded in the lysosome. In some embodiments, the heterologous polypeptide is a light immunoglobulin chain. In some embodiments, the heterologous polypeptide is a heavy immunoglobulin chain. In some embodiments, the heterologous polypeptide is a heavy single heavy chain variable domain of antibodies of the type that can be found in Camelid mammals which are naturally devoid of light chains.

Particularly, in the context of the invention, the antibody is a single domain antibody. The term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 1" or "CDR2" and as "Complementarity Determining Region 2" or "CDR3" and as "Complementarity Determining Region 2", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (http://imgt.cines.fr/).

Particularly, in the context of the invention, the antibody is a single chain variable fragment. The term "single chain variable fragment" or "scFv fragment" refers to a single folded polypeptide comprising the VH and VL domains of an antibody linked through a linker molecule. In such a scFv fragment, the VH and VL domains can be either in the VH-linker-VL or VL-linker-VH order. In addition to facilitate its production, a scFv fragment may contain a tag molecule linked to the scFv via a spacer. A scFv fragment thus comprises the VH and VL domains implicated into antigen recognizing but not the immunogenic constant domains of corresponding antibody.

In one embodiment of the invention, the CD31$^{shed}$ ligand is a peptide.

The peptide is preferably a peptide as disclosed in WO2010/000741 or WO2013/190014.

Preferably, the CD31$^{shed}$ ligand is a synthetic peptide.

By a "synthetic peptide", it is intended that the peptide is not present within a living organism, e.g. within human body.

The synthetic peptide is preferably purified.

The synthetic peptide may be part of a composition or a kit.

The peptide may be selected in the group consisting of:
(i) a peptide consisting of a fragment of 3 to 15 amino acids of the sequence defined by amino acids 579 to 601 of sequence SEQ ID NO: 1,
(ii) a peptide consisting of a fragment of 3 to 15 amino acids of a sequence corresponding to the amino acids 579 to 601 of sequence SEQ ID NO: 1 in a non-human mammalian CD31,
(iii) a peptide of 3 to 15 amino acids consisting of a sequence at least 70% identical to the sequence of peptide (i),
(iv) a peptide consisting of a retro-inverso sequence of peptide (i), (ii) or (iii), and
(v) the peptide (i), (ii), (iii) or (iv) comprising at least one or at least one further chemical modification, preferably at least one amino acid in the D-enantiomer form.

A "fragment" refers herein to a sequence of consecutive amino acids. For example, a fragment may be a fragment of 3, 4, 5, 6, 7, 8, 9, 10, 11, 12, 13, 14 or 15 amino acids.

The sequence defined by amino acids 579 to 601 of sequence SEQ ID NO: 1 is sequence SEQ ID NO: 12.

Thus, the peptide may consist of a fragment of 3 to 15 amino acids of sequence SEQ ID NO: 12.

The peptide may also consist of a fragment of 3 to 15 amino acids of a sequence corresponding to sequence SEQ ID NO: 12 in a non-human mammalian CD31.

Non-limiting examples of non-human mammalian CD31 are the murine CD31 of sequence SEQ ID NO: 9, the bovine CD31 of sequence SEQ ID NO: 10 and the pig CD31 of sequence SEQ ID NO: 11.

The person skilled in the art can easily identify a sequence corresponding to the amino acids 579 to 601 of sequence SEQ ID NO: 1, i.e. to sequence SEQ ID NO: 12, in a non-human mammalian CD31 protein, for example by performing a sequence alignment between sequence SEQ ID NO: 1 and the sequence of said non-human mammalian CD31 protein, for example with one of sequences SEQ ID NO: 9, SEQ ID NO: 10 and SEQ ID NO: 11.

Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

The sequence of the CD31 peptide according to the invention is preferably derived from the sequence of human CD31 or murine CD31.

The peptide may also be a peptide of 3 to 15 amino acids consisting of a sequence at least 70%, at least 75%, at least 80%, at least 85% or at least 90% identical to the sequence of peptide (i), i.e. to the sequence of a fragment of 3 to 15 amino acids of the sequence defined by amino acids 579 to 601 of sequence SEQ ID NO: 1.

A peptide sequence at least 70% identical to a given sequence of 4 to 6 amino acids differs from said given sequence of at most one amino acid.

A peptide sequence at least 70% identical to a given sequence of 7 to 9 amino acids differs from said given sequence of at most two amino acids.

A peptide sequence at least 70% identical to a given sequence of 10 to 13 amino acids differs from said given sequence of at most three amino acids.

A peptide sequence at least 70% identical to a given sequence of 14 or 15 amino acids differs from said given sequence of at most four amino acids.

By "a sequence at least x % identical to a reference sequence", it is intended that the amino acid sequence of the subject peptide is identical to the reference sequence or differ from the reference sequence by up to 100-x amino acid alterations per each 100 amino acids of the reference sequence. In other words, to obtain a polypeptide having an amino acid sequence at least x % identical to a reference amino acid sequence, up to 100-x % of the amino acid residues in the subject sequence may be inserted, deleted or substituted with another amino acid.

Methods for comparing the identity of two or more sequences are well known in the art. For instance, programs available in the Wisconsin Sequence Analysis Package, version 9.1, for example the programs BESTFIT and GAP, may be used to determine the % identity between two polypeptide sequences. BESTFIT uses the "local homology" algorithm of Smith and Waterman and finds the best single region of similarity between two sequences. Other programs for determining identity between sequences are also known in the art, for instance the Needle program, which is based on the Needleman and Wunsch algorithm, described in Needleman and Wunsch (1970) J. Mol Biol. 48:443-453, with for example the following parameters for polypeptide sequence comparison: comparison matrix: BLOSUM62, gap open penalty: 10 and gap extend penalty: 0.5, end gap penalty: false, end gap open penalty=10, end gap extend penalty=0.5; and the following parameters for polynucleotide sequence comparison: comparison matrix: DNA-FULL; gap open penalty=10, gap extend penalty=0.5, end gap penalty: false, end gap open penalty=10, end gap extend penalty=0.5.

Peptides consisting of an amino acid sequence "at least 70%, 75%, 80%, 85%, or 90% identical" to a reference sequence may comprise mutations, such as deletions, insertions and/or substitutions compared to the reference sequence.

In case of substitutions, the substitution preferably corresponds to a conservative substitution as indicated in the Table 1 below. In a preferred embodiment, the peptide consisting of an amino acid sequence at least 70%, 75%, 80%, 85% or 90% identical to a reference sequence only differs from the reference sequence by conservative substitutions.

TABLE 1

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

In another preferred embodiment, the peptide consisting of an amino acid sequence at least 70%, 75%, 80%, 85% or 90% identical to a reference sequence corresponds to a naturally-occurring allelic variant of the reference sequence.

In still another preferred embodiment, the peptide consisting of an amino acid sequence at least 70%, 75%, 80%, 85% or 90% identical to a reference sequence corresponds to a homologous sequence derived from another non-human mammalian species than the reference sequence.

In a preferred embodiment, the peptide consisting of an amino acid sequence at least 70%, 75%, 80%, 85% or 90% identical to a reference sequence differs from the reference sequence by conservative substitutions and/or corresponds to a homologous sequence derived from another non-human mammalian species than the reference sequence.

By the expression "a peptide consisting of a retro-inverso sequence of peptide (i), (ii) or (iii)", it is herein meant a peptide that differs from the peptide (i), (ii) or (iii) in that its amino acids are in the reverse order by comparison to the sequence of peptide (i), (ii) or (iii), respectively, and consist of D-amino acids instead of the naturally-occurring L-amino acids.

D-enantiomers of amino acids (also called D-amino acids) are referred to by the same letter as their corresponding L-enantiomer (also called L-amino acid), but in lower case. Thus, for example, the L-enantiomer of arginine is referred to as 'IR', while the D-enantiomer is referred to as 'r'.

Preferably, the peptide is soluble in an organic or nonorganic solvent.

In a preferred embodiment, the peptide is soluble in water. More particularly, the peptide is preferably soluble in water and/or in aqueous buffer such as trifluoroacetate (for example in a 0.1% trifluoroacetate solution), NaCl 9 g/L, PBS, Tris or Tris-phosphate. The solubility in water and aqueous buffers is particularly advantageous on the pharmacological point of view. Thanks to such solubility, the peptide may be dissolved in an aqueous solution, for example at a concentration equal to, at least of or at most of 1 micromolar, 10 micromolar, 50 micromolar, 100 micromolar, 500 micromolar, 1 mM, 50 mM or 100 mM.

A $CD31^{shed}$ ligand of the invention that is readily soluble in water may be obtained by the presence of at least one charged amino acid (preferably arginine (R) and/or lysine (K)), wherein said charged amino acid is not comprised between two hydrophobic residues.

Thus, in a preferred embodiment, the $CD31^{shed}$ ligand according to the invention comprises at least one charged amino acid, preferably arginine and/or lysine, wherein said charged amino acid is not comprised between two hydrophobic residues.

In a more preferred embodiment, said charged amino acid is located either at the N- or C-terminal end of the sequence.

For example, the sequence of a preferred $CD31^{shed}$ ligand according to the invention begins with the motif RV (for example instead of VRV).

In a preferred embodiment, the peptide is resistant to peptidase, in particular to eukaryote peptidase.

By "resistant to peptidase", it is herein meant that the $CD31^{shed}$ ligand remains undigested, as determined by reverse phase-high-performance liquid chromatography (RP-HPLC) and mass spectroscopy (MS), upon incubation at 37° C. with mammalian serum or injection in a living laboratory animal. Laboratory tests aimed at evaluating serum stability of the peptides are well standardized (see for example Jenssen and Aspmo, 2008, Methods Mol Biol 494, 177-186). Highly peptidase-resistant peptides are those that remains undigested for up to 70% of their original mass and/or displaying a half life longer than 240 minutes in the presence of proteolytic enzymes (see for example Kumarasinghe and Hruby, 2015, In Peptide Chemistry and Drug Design, B. M. Dunn, ed. (Hoboken, N.J.: Wiley), pp. 247-266).

The CD31$^{shed}$ ligand is preferably resistant to peptidases present in blood, such as soluble peptidases or peptidases present on cell surface.

The CD31$^{shed}$ ligand may also comprise at least one or at least one further chemical modification, preferably to improve its stability and/or bioavailability.

Such chemical modifications generally aim at obtaining peptides with increased protection of the peptides against enzymatic degradation in vivo and/or increased capacity to cross membrane barriers, thus increasing its half-life and/or maintaining or improving its biological activity. Any chemical modification known in the art can be employed according to the present invention.

The CD31$^{shed}$ ligand may comprise at least one artificial amino acid, said artificial amino acid being preferably selected from the group consisting of a D-enantiomer amino acid, a beta-methyl amino acid, a alpha-substituted alpha-amino acid and an amino acid analog.

By "beta-methyl amino acid", it is herein meant a derivative of the amino acid alanine with an aminomethyl group on the side chain. This non-proteinogenic amino acid is classified as a polar base.

By "alpha-substituted alpha-amino acid", it is herein meant that the group on the alpha carbon of an L-amino acid (NH2) has been changed to another, non proteinaceous group, such as a methyl-, aryl- or acyl-group.

By "amino acid analog", it is herein meant any other artificial analog of a natural amino acid.

The CD31$^{shed}$ ligand may thus comprise at least one amino acid in the D-enantiomer form. For example, 1, 2, 3, 4, 5, 6, 7, 8, 9, 10, 11, 12, 13, 14 or 15 of the amino acids of the CD31$^{shed}$ ligand defined above may be in the D-enantiomer form.

In one embodiment, the CD31$^{shed}$ ligand consists of D-amino acids.

The CD31$^{shed}$ ligand may also comprise an inverted sequence, namely an inversion of the amino acid chain (from the C-terminal end to the N-terminal end). The entire amino acid sequence of the peptide may be inverted, or a portion of the amino acid sequence may be inverted. For example, a consecutive sequence of 2, 3, 4, 5, 6, 7, 8, 9, 10, 11, 12, 13, 14 or 15 amino acids may be inverted. Reference herein to 'inverted' amino acids refers to inversion of the sequence of consecutive amino acids in the sequence.

Other chemical modifications include, but are not limited to:
- modifications to the N-terminal and/or C-terminal ends of the peptides such as e.g. N-terminal methylation, N-terminal acylation (preferably acetylation) or deamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids;
- retro-inversions in which one or more naturally-occurring amino acids (L-enantiomer) are replaced with the corresponding D-enantiomers, together with an inversion of the amino acid chain (from the C-terminal end to the N-terminal end);
- azapeptides, in which one or more alpha carbons are replaced with nitrogen atoms; betapeptides, in which the amino group of one or more amino acid is bonded to the β carbon rather than the α carbon,
- ester linkage(s) (such as α-hydroxy acid(s)),
- insertion of extra methylene group(s) (for example β- and γ-amino acid(s), and/or
- Peptoid(s), oligourea(s), arylamide(s) and/or oligohydrazide(s).

The CD31$^{shed}$ ligand includes amino acids modified either by natural processes, such as post-translational processing, or by chemical modification techniques which are well known in the art. Such modifications are well described in basic texts and in more detailed monographs, as well as in a voluminous research literature. Modification(s) can occur anywhere in a polypeptide, including the peptide backbone, the amino acid side-chains and the amino or carboxyl termini, it will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural post-translational processes or may be made by synthetic methods. Modifications include acetylation, acylation, ADP-ribosylation, araidation, covalent attachment of flavin, covalent attachment of a heme moiety, covalent attachment of a nucleotide or nucleotide derivative, covalent attachment of a lipid or lipid derivative, covalent attachment of phosphatidyl inositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, mefhylation, myristoylation, oxidation, proteolytic processing, phosphorylation, prenylation, racemization, selenoyiation, sulfation, transfer-RNA mediated addition of amino acids to proteins such as arginylation, and ubiquitination.

In a preferred embodiment of the invention, the CD31$^{shed}$ ligand is selected in the group consisting of:
(i) a peptide consisting of a fragment of 3 to 15 amino acids of the sequence defined by amino acids 579 to 601 of sequence SEQ ID NO: 1, said fragment comprising the amino acids 579 to 581, the amino acids 589 to 591, the amino acids 599 to 601 and/or the amino acids 593 to 595 of SEQ ID NO: 1,
(ii) a peptide consisting of a fragment of 3 to 15 amino acids of a sequence corresponding to the amino acids 579 to 601 of sequence SEQ ID NO: 1 in a non-human mammalian CD31, for example a fragment of 3 to 15 amino acids of the sequence defined by amino acids 568 to 590 of sequence SEQ ID NO: 9, said fragment preferably comprising the amino acids 568 to 570, the amino acids 578 to 580, the amino acids 588 to 590 and/or the amino acids 582 to 584 of SEQ ID NO: 9,
(iii) a peptide of 3 to 15 amino acids consisting of a sequence at least 70% identical, preferably at least 75% identical, preferably at least 80% identical, more preferably at least 85% identical, still more preferably at least 90% identical to the sequence of peptide (i),
(iv) a peptide consisting of a retro-inverso sequence of peptide (i), (ii) or (iii), and (v) the peptide (i), (ii), (iii) or (iv) comprising at least one or at least one further chemical modification.

Such peptide has, for example, a sequence selected from the group consisting of: SSTLAVRVFLAPWKK (SEQ ID NO: 13, amino acids 576 to 590 of SEQ ID NO: 9), STLAVRVFLAPWKK (SEQ ID NO: 14, amino acids 577 to 590 of SEQ ID NO: 9), TLAVRVFLAPWKK (SEQ ID NO: 15, amino acids 578 to 590 of SEQ ID NO: 9), LAVRVFLAPWKK (SEQ ID NO: 16, amino acids 579 to 590 of SEQ ID NO: 9), AVRVFLAPWKK (SEQ ID NO: 17, amino acids 580 to 590 of SEQ ID NO: 9), VRVFLAPWKK (SEQ ID NO: 3, amino acids 581 to 590 of SEQ ID NO: 9), RVFLAPWKK (SEQ ID NO: 18, amino acids 582 to 590 of SEQ ID NO: 9), VFLAPWKK (SEQ ID NO: 19, amino acids 583 to 590 of SEQ ID NO: 9), FLAPWKK (SEQ ID NO: 20, amino acids 584 to 590 of SEQ ID NO: 9), LAPWKK (SEQ ID NO: 2, amino acids 585 to 590 of SEQ ID NO: 9), APWKK (SEQ ID NO: 21, amino acids 586 to 590 of SEQ ID NO: 9), PWKK (SEQ ID NO: 22, amino acids 587 to 590 of SEQ ID NO: 9), WKK (amino acids 588 to 590 of SEQ ID NO: 9), SKILTVRVILAPWKK (SEQ ID NO: 23, amino acids 587 to 601 of SEQ ID NO: 1), KILTVRVILAPWKK (SEQ ID NO: 24, amino acids 588 to 601 of SEQ ID NO: 1), ILTVRVILAPWKK (SEQ ID NO: 25, amino acids 589 to 601 of SEQ ID NO: 1), LTVRVILAPWKK (SEQ ID NO: 26, amino acids 590 to 601 of SEQ ID NO: 1), TVRVILAPWKK (SEQ ID NO: 27, amino acids 591 to 601 of SEQ ID NO: 1), VRVILAPWKK (SEQ ID NO: 4, amino acids 592 to 601 of SEQ ID NO: 1), RVILAPWKK (SEQ ID NO: 28, amino acids 593 to 601 of SEQ ID NO: 1), VILAPWKK (SEQ ID NO: 29, amino acids 594 to 601 of SEQ ID NO: 1), ILAPWKK (SEQ ID NO: 30, amino acids 595 to 601 of SEQ ID NO: 1), SSMRTSPRSSTLAVR (SEQ ID NO: 31, amino acids 568 to 582 of SEQ ID NO: 9), SSMRTSPRSSTLAV (SEQ ID NO: 32, amino acids 568 to 581 of SEQ ID NO: 9), SSMRTSPRSSTLA (SEQ ID NO: 33, amino acids 568 to 580 of SEQ ID NO: 9), SSMRTSPRSSTL (SEQ ID NO: 34, amino acids 568 to 579 of SEQ ID NO: 9), SSMRTSPRSST (SEQ ID NO: 35, amino acids 568 to 578 of SEQ ID NO: 9), SSMRTSPRSS (SEQ ID NO: 36, amino acids 568 to 577 of SEQ ID NO: 9), SSMRTSPRS (SEQ ID NO: 37, amino acids 568 to 576 of SEQ ID NO: 9), SSMRTSPR (SEQ ID NO: 38, amino acids 568 to 575 of SEQ ID NO: 9), SSMRTSP (SEQ ID NO: 39, amino acids 568 to 574 of SEQ ID NO: 9), SSMRTS (SEQ ID NO: 40, amino acids 568 to 573 of SEQ ID NO: 9), SSMRT (SEQ ID NO: 41, amino acids 568 to 572 of SEQ ID NO: 9), SSMR (SEQ ID NO: 42, amino acids 568 to 571 of SEQ ID NO: 9), SSM (amino acids 568 to 570 of SEQ ID NO: 9), NHASSVPRSKILTVR (SEQ ID NO: 43, amino acids 579 to 593 of SEQ ID NO: 1), NHASSVPRSKILTV (SEQ ID NO: 44, amino acids 579 to 592 of SEQ ID NO: 1), NHASSVPRSKILT (SEQ ID NO: 45, amino acids 579 to 591 of SEQ ID NO: 1), NHASSVPRSKIL (SEQ ID NO: 46, amino acids 579 to 590 of SEQ ID NO: 1), NHASSVPRSKI (SEQ ID NO: 47, amino acids 579 to 589 of SEQ ID NO: 1), NHASSVPRSK (SEQ ID NO: 48, amino acids 579 to 588 of SEQ ID NO: 1), NHASSVPRS (SEQ ID NO: 49, amino acids 579 to 587 of SEQ ID NO: 1), NHASSVPR (SEQ ID NO: 50, amino acids 579 to 586 of SEQ ID NO: 1), NHASSVP (SEQ ID NO: 51, amino acids 579 to 585 of SEQ ID NO: 1), NHASSV (SEQ ID NO: 52, amino acids 579 to 584 of SEQ ID NO: 1), NHASS (SEQ ID NO: 53, amino acids 579 to 583 of SEQ ID NO: 1), NHAS (SEQ ID NO: 54, amino acids 579 to 582 of SEQ ID NO: 1), NHA (amino acids 579 to 581 of SEQ ID NO: 1), TSPRSSTLAVRVFLA (SEQ ID NO: 55, amino acids 572 to 586 of SEQ ID NO: 9), SPRSSTLAVRVFL (SEQ ID NO: 56, amino acids 573 to 585 of SEQ ID NO: 9), PRSSTLAVRVF (SEQ ID NO: 57, amino acids 574 to 584 of SEQ ID NO: 9), RSSTLAVRV (SEQ ID NO: 58, amino acids 575 to 583 of SEQ ID NO: 9), SSTLAVR (SEQ ID NO: 59, amino acids 576 to 582 of SEQ ID NO: 9), STLAV (SEQ ID NO: 60, amino acids 577 to 581 of SEQ ID NO: 9), TLA (amino acids 578 to 580 of SEQ ID NO: 9), SVPRSKILTVRVILA (SEQ ID NO: 61, amino acids 583 to 597 of SEQ ID NO: 1), VPRSKILTVRVIL (SEQ ID NO: 62, amino acids 584 to 596 of SEQ ID NO: 1), PRSKILTVRVI (SEQ ID NO: 63, amino acids 585 to 595 of SEQ ID NO: 1), RSKILTVRV (SEQ ID NO: 64, amino acids 586 to 594 of SEQ ID NO: 1), SKILTVR (SEQ ID NO: 65, amino acids 587 to 593 of SEQ ID NO: 1), KILTV (SEQ ID NO: 66, amino acids 588 to 562 of SEQ ID NO: 1), ILT (amino acids 589 to 591 of SEQ ID NO: 1), RVF (amino acids 582 to 584 of SEQ ID NO: 9), RVFL (SEQ ID NO: 67, amino acids 582 to 585 of SEQ ID NO: 9), RVFLA (SEQ ID NO: 68, amino acids 582 to 586 of SEQ ID NO: 9), RVFLAP (SEQ ID NO: 69, amino acids 582 to 587 of SEQ ID NO: 9), RVFLAPW (SEQ ID NO: 70, amino acids 582 to 588 of SEQ ID NO: 9), RVFLAPWK (SEQ ID NO: 5, amino acids 582 to 589 of SEQ ID NO: 9), RVI (amino acids 593 to 595 of SEQ ID NO: 1), RVIL (SEQ ID NO: 71, amino acids 593 to 596 of SEQ ID NO: 1), RVILA (SEQ ID NO: 72, amino acids 593 to 597 of SEQ ID NO: 1), RVILAP (SEQ ID NO: 73, amino acids 593 to 598 of SEQ ID NO: 1), RVILAPW (SEQ ID NO: 74, amino acids 593 to 599 of SEQ ID NO: 1), RVILAPWK (SEQ ID NO: 7, amino acids 593 to 600 of SEQ ID NO: 1).

In a more preferred embodiment of the invention, the CD31$^{shed}$ ligand is selected in the group consisting of:
(i) a peptide consisting of a fragment of 3 to 15 amino acids of the sequence defined by amino acids 579 to 601 of sequence SEQ ID NO: 1, said fragment comprising the amino acids 579 to 582, the amino acids 588 to 592, the amino acids 598 to 601 and/or the amino acids 593 to 595 of SEQ ID NO: 1,
(ii) a peptide consisting of a fragment of 3 to 15 amino acids of a sequence corresponding to the amino acids 579 to 601 of sequence SEQ ID NO: 1 in a non-human mammalian CD31, for example a fragment of 3 to 15 amino acids of the sequence defined by amino acids 568 to 590 of sequence SEQ ID NO: 9, said fragment preferably comprising the amino acids 568 to 571, the amino acids 578 to 580 the amino acids 587 to 590 and/or the amino acids 582 to 584 of SEQ ID NO: 9,
(iii) a peptide of 3 to 15 amino acids consisting of a sequence at least 70% identical, preferably at least 75% identical, preferably at least 80% identical, more preferably at least 85% identical, still more preferably at least 90% identical to the sequence of peptide (i),
(iv) a peptide consisting of a retro-inverso sequence of peptide (i), (ii) or (iii), and
(v) the peptide (i), (ii), (iii) or (iv) comprising at least one or at least one further chemical modification.

In a preferred embodiment, the CD31$^{shed}$ ligand is an 8 amino-acid fragment comprising inversions and/or at least one unnatural amino acid, such as at least one D-amino acids. Such peptides indeed retain the activity of the original peptide or even demonstrate improved activity. Incorporation of unnatural amino acids in peptides intended for therapeutic use is of utility in increasing the stability of the peptide, in particular in vivo stability.

In another preferred embodiment of the invention, the CD31$^{shed}$ ligand is selected in the group consisting of a peptide of sequence SEQ ID NO: 2, a peptide of sequence SEQ ID NO: 3, a peptide of sequence SEQ ID NO: 4, a peptide of sequence SEQ ID NO: 5, a peptide of sequence SEQ ID NO: 6 consisting of D-enantiomer amino acids, a peptide of sequence SEQ ID NO: 7 and a peptide of sequence SEQ ID NO: 8 consisting of D-enantiomer amino acids.

A more preferred CD31$^{shed}$ ligand is a peptide of sequence SEQ ID NO: 5 or a peptide of sequence SEQ ID NO: 6 consisting of D-enantiomer amino acids.

The CD31$^{shed}$ ligand may additionally comprise at least one chelating agent.

A chelating agent is a molecule covalently bound to the ligand, which allows complexing radiometal(s).

Typically, chelating agents could be: 6-Hydrazinopyridine-3-carboxylic acid (HYNIC), chelating peptide such as Gly-Gly-Cys or His-based sequence (Francesconi 2004, Waibel 1999, Ali 2011), MAG3 en N-ter (Okarvi 2012, 2004), 1,4,7,10-tetraazacyclododecane-1,4,7,10-tetracetic acid (DOTA), diethylene triamine penta-acetic acid (DTPA), 1,4,7-tris(carboxymethylaza)cyclododecane-10-azaacetylamide (DO3A), nitrilotriacetic acid (NTA), D-penicillamine, 2,3-dimercaptosuccinic acid,2,3-dimercapto-1-propanesulfonic acid, 2,3-dimercaptopropanol (BAL), triethylenetetramine, ammonium tetrathiomolybdate anion, ethylenediaminetetraacetic acid (EDTA), 2-(p-isothiocyanatobenzyl)-6-methyldiethylenetriaminepentaacetic acid (IB4M) or hydroxypyridinone (HOPO).

The CD31$^{shed}$ ligand may be linked to the chelating agent directly (for example the chelating agent being attached to a lateral amino acid long chain) or indirectly, for example via at least one spacer.

A preferred chelating agent is 6-Hydrazinopyridine-3-carboxylic acid (HYNIC).

In such case, the peptide of the CD31$^{shed}$ ligand may be linked to HYNIC directly (for example HYNIC being attached to a lateral amino acid long chain) or indirectly, for example via at least one spacer.

The spacer for example comprises or consists of at least one PEG (polyethylene glycol), for example one, two or at least three PEG, more preferably three PEG and/or at least one aliphatic spacer.

A preferred CD31$^{shed}$ ligand is a compound of the following formula:

This compound is also called HYNIC-P8RI in the following.

The CD31$^{shed}$ ligand may be prepared by any well-known procedure in the art, such as chemical synthesis, for example solid phase synthesis or liquid phase synthesis, or genetic engineering. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. After synthesis of the desired peptide, it is subjected to the deprotection reaction and cut out from the solid support. Such peptide cutting reaction may be carried with hydrogen fluoride or tri-fluoromethane sulfonic acid for the Boc method, and with TFA for the Fmoc method.

Solid phase synthesis methods are largely classified by the tBoc method and the Fmoc method, depending on the type of protective group used. Typically used protective groups include tBoe (t-butoxycarbonyl), CI-Z (2-chlorobenzyloxycarbonyl), Br-Z (2-bromobenzyloyycarbonyl), Bzl (benzyl), Fmoc (9-fluorenylmcthoxycarbonyl), Mbh (4, 4'-dimethoxydibenzhydryl), Mtr (4-methoxy-2, 3, 6-trimethylbenzenesulphonyl), Trt (trityl), Tos (tosyl), Z (benzyloxycarbonyl) and Clz-Bzl (2, 6-dichlorobenzyl) for the amino groups; NO2 (nitro) and Pmc (2,2, 5,7, 8-pentamethylchromane-6-sulphonyl) for the guanidino groups); and tBu (t-butyl) for the hydroxyl groups).

Alternatively, the CD31$^{shed}$ ligand may be synthesized using recombinant techniques.

The method of producing the CD31$^{shed}$ ligand may optionally comprise the steps of purifying said CD31$^{shed}$ ligand, chemically modifying said CD31$^{shed}$ ligand, and/or formulating said CD31$^{shed}$ ligand into a pharmaceutical composition.

In an embodiment, the CD31$^{shed}$ ligand is a peptidomimetic of a peptide as defined above, i.e. a compound that mimics said peptide.

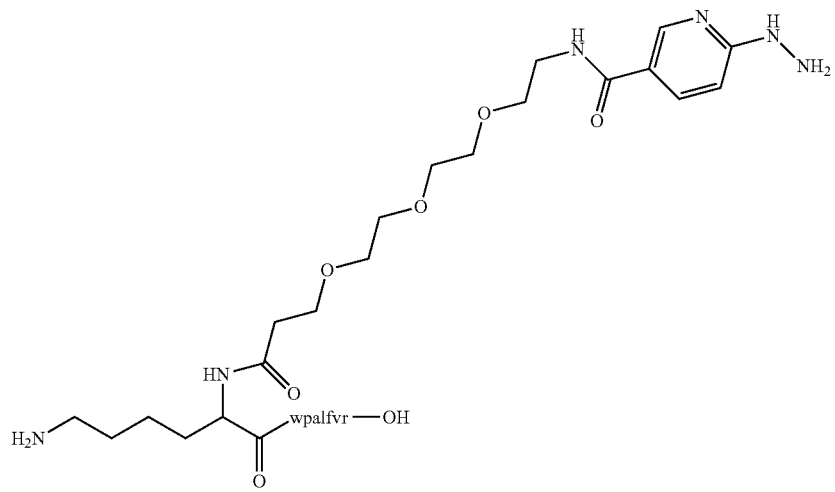

A «peptidomimetic» is a compound consisting of or essentially consisting of non-peptidic structural elements that mimics a given peptide, thereby conferring to said compound a biological activity equal to or similar to said peptide.

The peptidomimetic is preferably soluble in an organic or nonorganic solvent.

As the peptide previously, the peptidomimetic is preferably soluble in water.

Methods for designing and synthesizing peptidomimetics of a given peptide are well-known in the art and include e.g. those described in Ripka and Rich (Curr. Opin. Chem. Biol. 1998; 2(4):441-52) and in Patch and Barron (Curr. Opin. Chem. Biol. 2002; 6(6):872-7).

Imaging Label

The labeled $CD31^{shed}$ ligand according to the invention comprises at least one imaging label.

Said imaging label may be a radionucleide or a contrastophor.

The term "contrastophor" as used herein refers to a contrast agent, for example comprising a chelating agent.

Examples of chelating agent that may be used in a contrastophor are given below in the section "$CD31^{shed}$ ligand".

Non-limitative examples of contrastophor are Gd-DTPA (complex of gadolinium and DTPA) or Gd-DOTA (complex of gadolinium and DOTA).

A contrastophor is preferably used in MRI (also called thereafter "IRM" or "Magnetic Resonance Imaging").

The term "radionuclide" as used herein has the same meaning as radioactive nuclide, radioisotope or radioactive isotope.

The radionuclide is preferably detectable by nuclear medicine molecular imaging technique(s), such as, Positron Emission Tomography (PET), Single Photon Emission Computed Tomography (SPECT), an hybrid of SPECT and/or PET or their combinations.

Single Photon Emission Computed Tomography (SPECT) herein includes planar scintigraphy (PS).

An hybrid of SPECT and/or PET is for example SPECT/CT, PET/CT, PET/IRM or SPECT/IRM.

SPECT and PET acquire information on the concentration (or uptake) of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver, . . . ). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Actual clinical PET presents higher sensitivity and better spatial resolution than SPECT, and presents the advantage of an accurate attenuation correction due to the high energy of photons; so PET provides more accurate quantitative data than SPECT. Planar scintigraphy (PS) is similar to SPECT in that it uses the same radionuclides. However, PS only generates 2D-information.

SPECT produces computer-generated images of local radiotracer uptake, while CT produces 3-D anatomic images of X ray density of the human body. Combined SPECT/CT imaging provides sequentially functional information from SPECT and the anatomic information from CT, obtained during a single examination. CT data are also used for rapid and optimal attenuation correction of the single photon emission data. By precisely localizing areas of abnormal and/or physiological tracer uptake, SPECT/CT improves sensitivity and specificity, but can also aid in achieving accurate dosimetric estimates as well as in guiding interventional procedures or in better defining the target volume for external beam radiation therapy. Gamma camera imaging with single photon emitting radiotracers represents the majority of procedures.

In a preferred embodiment, the radionuclide is detectable by SPECT or an hybrid SPECT/CT.

The radionuclide may be selected in the group consisting of technetium-99m ($^{99m}Tc$), gallium-67 ($^{67}Ga$), gallium-68 ($^{68}Ga$) yttrium-90 ($^{90}Y$), indium-111 ($^{111}In$), rhenium-186 ($^{186}Re$), fluorine-18 ($^{18}F$), copper-64 ($^{64}Cu$) or thallium-201 ($^{201}Tl$).

A preferred radionuclide is technetium-99m (99mTc).

Labeled $CD31^{shed}$ Ligand

The present invention thus particularly relates to a labeled $CD31^{shed}$ ligand comprising a $CD31^{shed}$ ligand and at least one imaging label.

The $CD31^{shed}$ ligand and the imaging label are as defined above in the sections of the same name.

The radiochemical specific activity of labeled $CD31^{shed}$ ligand is preferably greater than 70 GBq/µmol, more preferably greater than 80 GBq/µmol, more preferably greater than 90 GBq/µmol, for example greater than 100 GBq/µmol.

The labeled $CD31^{shed}$ ligand is preferably stable.

The stability of the labeled $CD31^{shed}$ ligand may be assessed in vitro and/or in vivo by any method well known by the skilled person, for example by determining radiochemical purity (RCP).

The radiochemical purity (RCP) may be assessed by high performance liquid chromatography (HPLC) and/or instant thin layer chromatography (ITLC), preferably using both methods.

For example, the in vitro stability may be assessed after incubation of the labeled $CD31^{shed}$ ligand in vitro in plasma, preferably in human plasma at 37° C., for example for at least 1 hour, at least 2 hours, at least 3 hours or at least 4 hours.

For example, the in vivo stability may be assessed in a sample of human or non-human mammal urine, for example of rat urine, after administration of the labeled $CD31^{shed}$ ligand in said human or non-human mammal.

The in vitro and/or in vivo RCP of the labeled $CD31^{shed}$ ligand is preferably greater than 80%, preferably greater than 85%, for example greater than 89%.

The biodistribution and specific uptake of the labeled $CD31^{shed}$ ligand by activated platelets, endothelial cells and leukocytes may be assessed in an inflammation model, for example in a rat model of heart inflammation, brain inflammation or vascular inflammation, such as the experimental abdominal aorta aneurysm (AAA) induced by local infusion of elastase and followed by intravenous injection of a periodontal bacterium present in human AAA and known to induce AAA inflammation. For example, immediately after intravenous injection of the labeled $CD31^{shed}$ ligand, sequential whole-body acquisitions (for example every 10 minutes for the first hour) are performed, for example using a hybrid SPECT/CT camera (NanoSPECT/CT, Bioscan Inc.).

The binding of the labeled $CD31^{shed}$ ligand to plasma proteins is preferably low, for example lower than 10%, more preferably lower than 5% after 4 hours of incubation in human plasma at 37° C.

The low binding to plasma proteins may be assessed by any method well known by the skilled person, such as size exclusion chromatography, for example after incubation of the labeled CD31$^{shed}$ ligand in vitro in plasma, preferably in human plasma, at 37° C., for example for at least 1 hour, at least 2 hours, at least 3 hours or at least 4 hours.

The CD31$^{shed}$ ligand and the imaging label may be linked covalently or non-covalently.

The CD31$^{shed}$ ligand and the imaging label are preferably linked non-covalently.

When the CD31$^{shed}$ ligand comprises a chelating agent, the CD31$^{shed}$ ligand is preferably linked to the imaging label via said chelating agent, and preferably non covalently.

The labeled CD31$^{shed}$ ligand is preferably a radiolabeled CD31$^{shed}$ ligand.

A preferred labeled CD31$^{shed}$ ligand thus comprises a CD31$^{shed}$ ligand and at least one radionuclide.

In one preferred embodiment of the invention, the labeled CD31$^{shed}$ ligand comprises a peptide of sequence SEQ ID NO: 6 consisting of D-enantiomer amino acids as CD31$^{shed}$ ligand and $^{99m}$Tc as a radionuclide.

The labeled CD31$^{shed}$ ligand may additionally comprise at least one co-ligand, i.e. one or more ligands coupled to the CD31$^{shed}$ ligand, The co-ligand(s) is/are preferably used to stabilize the imaging label binding to the CD31$^{shed}$ ligand.

For example, the co-ligand may be tricine, EDDA (ethylendiaminediacetic acid) (EDDA), aminocarboxylate, phosphine or pyridine.

In on embodiment, the labeled CD31$^{shed}$ ligand comprises both tricine and EDDA as co-ligands, for example when the radionuclide is 99mTc.

When at least one co-ligand is used, the labeled CD31$^{shed}$ ligand comprises or consists of a complex comprising said co-ligand(s), said CD31$^{shed}$ ligand and said radionuclide.

In one embodiment of the invention, the CD31$^{shed}$ ligand is the peptide of sequence SEQ ID NO: 6 consisting of D-enantiomer amino acids coupled with HYNIC via a spacer as defined above.

A preferred labeled CD31$^{shed}$ ligand, referred to as 99mTc-HYNIC-P8RI, comprises:

the compound of formula:

and the radionuclide 99mTc.

HYNIC forms a 99mTc-N bond between technetium and the hydrazine moiety of HYNIC.

The labeled CD31$^{shed}$ ligand can be prepared by conventional methods perfectly known by a man skilled in the art.

In the methods and uses described herein, the labeled CD31$^{shed}$ ligand may be used per se or as a pharmaceutical composition as defined below.

The methods and uses described herein may be performed by using a kit as defined below.

Labeled CD31$^{shed}$ Ligand for Use as a Molecular Imaging Agent

The present invention also relates to the use of a labeled CD31$^{shed}$ ligand as defined above as a molecular imaging agent for imaging inflammation sites.

The present invention thus also relates to a labeled CD31$^{shed}$ ligand as defined above for use as a molecular imaging agent for imaging of inflammatory sites.

The present invention particularly relates to a labeled CD31$^{shed}$ ligand as defined above for use as a molecular imaging agent in an in vivo method of detecting, more particularly imaging, inflammatory sites.

In particular, the present invention relates to a labeled CD31$^{shed}$ ligand for use as defined above, in a method, preferably an in vivo method, for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition.

The invention also relates to a labeled CD31$^{shed}$ ligand for use as defined above, wherein the presence, localization and/or amount of CD31$^{shed}$ is determined. The labeled CD31$^{shed}$ ligand indeed binds to CD31$^{shed}$.

The presence, localization and/or amount of CD31$^{shed}$ is determined by the presence, localization and/or amount of the labeled CD31$^{shed}$ ligand, i.e. of the signal detected corresponding to the imaging label of said labeled CD31$^{shed}$ ligand.

The presence, localization and/or amount of the labeled CD31$^{shed}$ ligand may be determined by planar scintigraphy

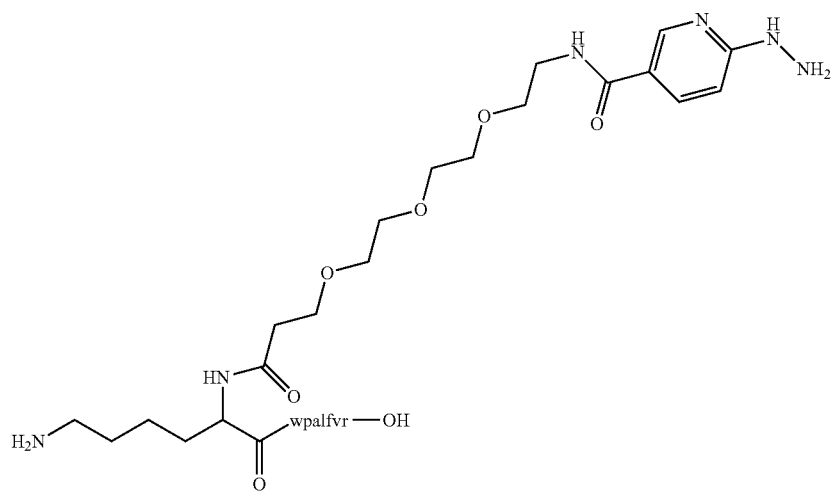

(PS), Positron Emission Tomography (PET), Single Photon Emission Computed Tomography (SPECT), an hybrid SPECT/CT or their combinations.

The labeled $CD31^{shed}$ ligand is preferably used or administered intravenously.

The labeled $CD31^{shed}$ ligand is preferably used or administered in an amount sufficient to obtain a detectable signal, in particular one injected intravenously.

The signal corresponding to the imaging label of the labeled $CD31^{shed}$ ligand is preferably detected immediately after the administration of the labeled $CD31^{shed}$ ligand.

The signal may be detected in the entire body of the subject or in only one part of the subject (particularly in only one part of the body of the subject).

The present invention thus particularly relates to a labeled $CD31^{shed}$ ligand as defined above for use in a method for detecting, more particularly imaging, inflammation sites, wherein said method comprises:
administering said labeled $CD31^{shed}$ ligand to the subject, and
imaging said subject or at least one part of the body of said subject, thereby detecting the binding of the labeled $CD31^{shed}$ ligand to $CD31^{shed}$ in said subject or in said part of the body of the subject.

The present invention thus particularly relates to a labeled $CD31^{shed}$ ligand as defined above for use in a method for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition, wherein said method comprises:
administering said labeled $CD31^{shed}$ ligand to the subject, and
imaging said subject or at least one part of the body of said subject, thereby detecting the binding of the labeled $CD31^{shed}$ ligand to $CD31^{shed}$ in said subject or in said part of the body of the subject.

The molecular imaging agent of the invention represents a powerful tool for diagnosing or assessing an inflammatory condition associated with $CD31^{shed}$.

a) Determining if a Subject Suffers from an Inflammatory or is at Risk of Suffering from an Inflammatory Condition.

In a method for determining whether a subject suffers from an inflammatory condition or is at risk of suffering from an inflammatory condition, the subject to be diagnosed is suspected to suffer or be likely to suffer from an inflammatory condition or suffers from an inflammatory condition. The method can indeed be performed to confirm that the subject suffers from an inflammatory condition and/or to specify the kind of inflammatory condition.

The presence, localization and/or amount of $CD31^{shed}$ may indicate that the subject suffers from an inflammatory condition.

The localization of $CD31^{shed}$ may further indicate the kind of inflammatory condition.

The amount of $CD31^{shed}$ may further indicate the severity of the inflammation condition.

The presence, localization and/or amount of $CD31^{shed}$ may be compared to a reference value or a control biological image. When the reference value or the control biological sample corresponds to a healthy subject, in particular a subject that does not suffer from an inflammatory condition or a panel of healthy subjects, a presence, localization and/or amount of $CD31^{shed}$ detected in the biological sample that is greater than those of reference value or of the control image indicates that the subject suffers or, is at risk of having an inflammatory condition.

b) Determining the Risk of Recurrence of an Inflammatory Condition after an Anti-Inflammatory Treatment The methods and uses according to the invention can also be used to follow the risk of recurrence of an inflammatory condition after an anti-inflammatory treatment. In particular, they can be used to monitor the subject after an anti-inflammatory treatment. For example, this can be achieved by repeating the method at least one time, preferably two times after the end of said treatment, in order to determine the presence, localization and/or amount of $CD31^{shed}$. An increased presence, localization and/or amount of $CD31^{shed}$ may indicate a high risk of recurrence of an inflammatory condition after an anti-inflammatory treatment. A stable or a decreased presence, localization and/or amount of $CD31^{shed}$ may indicate a low risk of recurrence of an inflammatory condition after an anti-inflammatory treatment. For example, an image of a biological sample and/or of the subject or at least one part of the subject is generated at the end of the treatment and at least one time after treatment. Comparison of the images at the end and after treatment allows the risk of recurrence of an inflammatory condition after an anti-inflammatory treatment to be monitored.

c) Monitoring the Response to a Treatment of a Subject Suffering from an Inflammatory Condition The methods and uses according to the invention can also be used to monitor the response to a treatment of a subject suffering from an inflammatory condition. For example, this can be achieved by repeating the method at least two times, for example one time before treatment and at least two times during the treatment, or at least two times during the treatment. For example, an image of a biological sample and/or of the subject or at least one part of the subject is generated before treatment and at least one time during the treatment, for example with an anti-inflammatory treatment. Comparison of the images before and during treatment allows the response of the subject to that particular treatment to be monitored.

An increased presence, localization and/or amount of $CD31^{shed}$ may indicate that the treatment is not or not any more efficient. A stable or a decreased presence, localization and/or amount of $CD31^{shed}$ may indicate that the treatment is efficient.

The expression "monitoring the response to a treatment" and "monitoring the efficacy of a treatment" are herein synonymous.

Said treatment may be a curative or preventive treatment.

Said treatment may comprise or consist in administering at least one anti-inflammatory agent, at least one immunosuppressant, at least one probiotic (i.e. live microorganisms that may confer a health benefit on the subject), at least one antibiotic or their combinations.

Method Using a Labeled $CD31^{shed}$ Ligand as a Molecular Imaging Agent

The present invention also relates to a method for imaging of inflammation sites using a labeled $CD31^{shed}$ ligand as defined above.

The present invention also relates to a method, preferably an in vitro method, for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition in a subject, wherein said method comprises detecting the presence of $CD31^{shed}$ on the surface of cells with a labeled $CD31^{shed}$ ligand as defined above in a biological sample of the subject.

The cells are preferably platelets, leukocytes and/or endothelial cells.

By "biological sample", it is herein meant any sample able to contain endothelial cells, platelets or leukocytes, such as a blood sample or fraction thereof (for example a thrombus) or a tissue sample, for example a biopsy.

The method may comprise a first step of providing a biological sample from the subject.

The present invention also relates to a method as defined above, wherein the detection of $CD31^{shed}$ on the surface of the cells in said biological sample indicates that the subject suffers, is at risk of having or developing an inflammatory condition or is at risk of recurrence of an inflammatory condition.

The present invention also relates to a method as defined above, wherein the amount of $CD31^{shed}$ detected on the surface of the cells in said biological sample is compared to a reference value or a control biological sample. When the reference value or the control biological sample corresponds to a healthy subject, in particular a subject that does not suffer from an inflammatory condition or a panel of healthy subjects, an amount of $CD31^{shed}$ detected in the biological sample that is greater than those of reference value or of the control biological sample indicates that the subject suffers, is at risk of having or developing an inflammatory condition or is at risk of recurrence of an inflammatory condition.

The present invention also relates to a method as defined above, wherein an increased amount of $CD31^{shed}$ detected on the surface of the cells in said biological sample by comparison to the amount detected in a biological sample before treatment or earlier during treatment indicates that said treatment is not efficient and/or wherein a stable or a decreased amount of $CD31^{shed}$ detected on the surface of the cells in said biological sample by comparison to the amount detected in a biological sample before treatment or earlier during treatment indicates that said treatment is efficient.

Said method may further comprise determining the amount of $CD31^{shed}$ on the surface of cells.

The detection of $CD31^{shed}$ on the surface of the cells in said biological sample is preferably carried out by imaging techniques.

The step of detection as mentioned above comprises contacting the biological sample of the subject with a labeled $CD31^{shed}$ ligand, preferably an effective amount of a labeled $CD31^{shed}$ ligand, as a molecular imaging agent.

The present invention also relates to a method as defined above, wherein said method comprises:
  contacting a biological sample of the subject with a labeled $CD31^{shed}$ ligand, and
  detecting the labeled $CD31^{shed}$ ligand bound to CD31 shed, thereby detecting the presence of $CD31^{shed}$ on the surface of cells in the biological sample.

The contact is preferably carried out under conditions that allow the molecular imaging agent (1) to reach the cells of the subject that may express $CD31^{shed}$ (preferably endothelial cells, platelets and/or leukocyte) and (2) to interact with such $CD31^{shed}$, so that the interaction results in the binding of the molecular imaging agent to the $CD31^{shed}$. After contact with the labeled $CD31^{shed}$ ligand and after sufficient time has elapsed for the interaction to take place, the molecular imaging agent bound to $CD31^{shed}$ present in the subject sample is detected by a molecular imaging technique as disclosed above.

An "effective amount" is an amount sufficient to allow the molecular imaging agent to complete these three conditions of (1) reaching the cells, (2) interacting with $CD31^{shed}$ and (3) being detected.

Method of Treatment of an Inflammation Condition

The present invention also relates to a method for preventing and/or treating an inflammatory condition in a subject in need thereof, wherein said method comprises,
  performing a method as defined above for determining whether a subject suffers from an inflammatory condition, is at risk of having an inflammatory condition or is at risk of recurrence of an inflammatory condition after an anti-inflammatory treatment or for monitoring the efficacy of a treatment of an inflammatory condition in a subject,
  when the subject is determined to suffer from an inflammatory condition, to be at risk of having an inflammatory condition or to be at risk of recurrence of an inflammatory condition after an anti-inflammatory treatment or if the treatment is not efficient, administering to said subject a suitable treatment.

Said suitable treatment may comprise or consist in administering at least one anti-inflammatory agent, at least one immunosuppressant, at least one probiotic (i.e. live microorganisms that may confer a health benefit on the subject), at least one antibiotic, at least one $CD31^{shed}$ ligand linked to an active ingredient or their combinations.

The present invention also relates to a method for preventing and/or treating an inflammatory condition in a subject in need thereof, wherein said method comprises administering to said subject a $CD31^{shed}$ ligand linked to an active ingredient.

The active ingredient is for example a drug, such as an anti-inflammatory agent. The $CD31^{shed}$ ligand is thereby used as a drug targeting agent and allows improving the effect of said drug.

Pharmaceutical Composition Comprising the Molecular Imaging Agent

The pharmaceutical composition according to the invention comprises at least one labeled $CD31^{shed}$ ligand and at least one pharmaceutically acceptable carrier.

As used herein, the term "pharmaceutically acceptable carrier" refers to a carrier medium which does not interfere with the effectiveness of the biological activity of the active ingredient, i.e. the molecular imaging agent, and which is not excessively toxic to the subject at the concentration(s) at which it is administered. This term includes solvent(s), dispersion medium/media, coating(s), antibacterial and/or antifungal agent(s), isotonic agent(s), adsorption delaying agent(s) and their combinations. The use of such medium/media and/or agent(s) for pharmaceutically active substance(s) is well known in the art.

The pharmaceutical composition may be administered by injection. For administration by injection, the pharmaceutical composition comprising the molecular imaging agent may be formulated as sterile aqueous or non-aqueous solution or alternatively as sterile powder for the extemporaneous preparation of a sterile injectable solution. The pharmaceutical composition should be stable under the conditions of manufacture and storage, and must be preserved against the contaminating action of microorganisms such as bacteria and fungi.

Pharmaceutically acceptable carrier(s) for administration by injection are solvent(s) or dispersion medium/media, such as aqueous solution(s) (e.g., Hank's solution, alcoholic/aqueous solution or saline solution), and non-aqueous carrier(s) (e.g. propylene glycol, polyethylene glycol, vegetable oil and injectable organic esters such as ethyl oleate). The injectable pharmaceutical composition may also contain parenteral vehicle(s) (such as sodium chloride and Ringer's dextrose) and/or intravenous vehicle(s) (such as fluid and nutrient replenishers); as well as other conventional, pharmaceutically acceptable, non-toxic excipient(s) and additive(s) including salt(s), buffer(s) and preservative(s) such as antibacterial and/or antifungal agent(s) (e.g. parabens, chlorobutanol, phenol, sorbic acid, thirmerosal and the like). Prolonged absorption of the injectable composition can be brought about by adding agents that can delay absorption (e.g. aluminum monostearate and/or gelatin). The pH and concentration of the various components can readily be determined by those skilled in the art.

The sterile injectable solution may be prepared by incorporating the active compound(s), i.e. the molecular imaging agent, and other ingredient(s) in the required amount of an appropriate solvent and then by sterilizing the resulting mixture, for example, by filtration and/or irradiation.

In general, the dosage of the molecular imaging agent (or pharmaceutical composition comprising thereof) will vary depending on considerations such as age, sex and weight of the subject, as well as the particular inflammatory condition suspected to affect the patient, the extent of the disease, the tissue(s) of the body to be examined and/or the sensitivity of the imaging label. Factors such as contraindications, therapies, and other variables are also to be taken into account to adjust the dosage of molecular imaging agent to be administered. This, however, can be readily achieved by a trained physician.

In general, one suitable dose of molecular imaging agent, i.e. of labeled $CD31^{shed}$ ligand, or a pharmaceutical composition comprising thereof, corresponds to the lowest amount of molecular imaging agent or pharmaceutical composition that is sufficient to allow molecular imaging of any relevant $CD31^{shed}$ present in the subject. To minimize this dose, it is preferred that administration be intravenous, intramuscular, intraperitoneal or subcutaneous, and preferably proximal to the site to be examined.

Kits

The present invention also provides a kit comprising material(s) useful for carrying out the methods and uses of the invention.

In certain embodiments, the kit comprises at least one $CD31^{shed}$ ligand as above described and at least one imaging label, preferably at least one radionuclide, and, optionally, instructions for associating said $CD31^{shed}$ ligand and said imaging label, preferably radionuclide, to form a labeled $CD31^{shed}$ ligand according to the invention.

The radionuclide is preferably a short-lived radionuclide, such as technetium-99m (99mTc), gallium-67 (67Ga), yttrium-90 (90Y), indium-111 (111In), rhenium-186 (186Re), and thallium-201 (201Tl), more preferably 99mTc.

In addition, the kit may further comprise at least one co-ligand, such as tricine and/or ethylendiaminediacetic acid (EDDA).

In addition, the kit may further comprise one or more of: labelling buffer, labelling reagent, purification buffer, purification reagent, purification means, injection medium, and/or injection reagent. Protocols for using these buffer(s), reagent(s) and/or means for performing different steps of the preparation procedure and/or administration may be included in the kit.

The different components included in the kit may be supplied in a solid (e.g. lyophilized) or liquid form.

The kit may optionally comprise different containers (e.g. vial, ampoule, test tube, flask or bottle) for each individual component. Each component will generally be suitable as aliquoted in its respective container or provided in a concentrated form. Other containers suitable for conducting certain steps of the preparation methods may also be provided. The individual containers of the kit are preferably maintained in close confinement for commercial sale.

In certain embodiments, the kit further comprises instructions for using its components for the imaging of an inflammatory condition as described herein, and in particular for determining whether a subject suffers from, is at risk of having or developing an inflammatory condition or is at risk of recurrence of an inflammatory condition after an anti-inflammatory treatment, as described herein.

Instructions for using the kit according to the invention may comprise instructions for preparing labeled $CD31^{shed}$ ligand from the $CD31^{shed}$ ligand and the imaging label, instructions concerning dosage and mode of administration of the molecular imaging agent thereby obtained, instructions for performing the detection of $CD31^{shed}$, and/or instructions for interpreting the results obtained. A kit may also contain a notice in the form prescribed by a governmental agency regulating the manufacture, use or sale of pharmaceuticals or biological products.

The present invention will be further illustrated in view of the following examples and figures.

All references cited herein, including journal articles or abstracts, published or unpublished patent application, issued patents or any other references, are entirely incorporated by reference herein, including all data, tables, figures and text presented in the cited references.

BRIEF DESCRIPTION OF THE SEQUENCES

Figure 1:
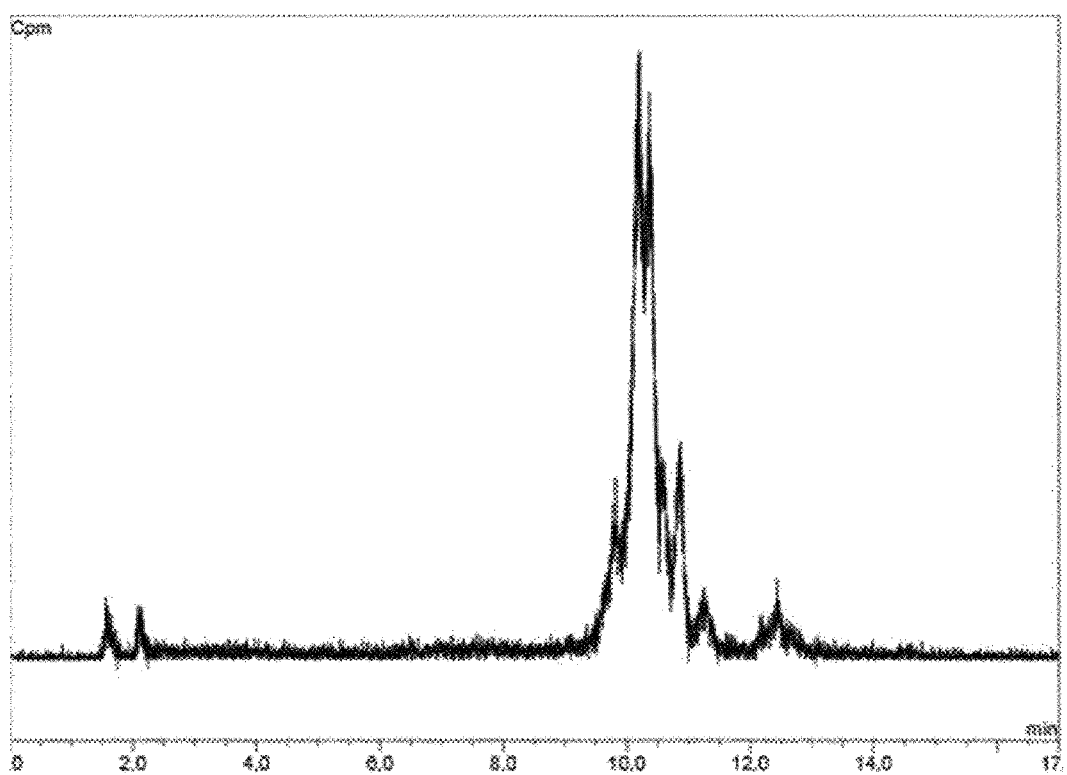
FIG. 1: Radio high performance liquid chromatography (HPLC) of 99mTc-HYNIC-P8RI with tricine (A) and tricine/EDDA as coligands (B). HPLC analysis of the acetonitrile fraction shows a major specie (Tr=10.1 min) with tricine/EDDA contrary to the multiple species profile with tricine.
Figure 1:
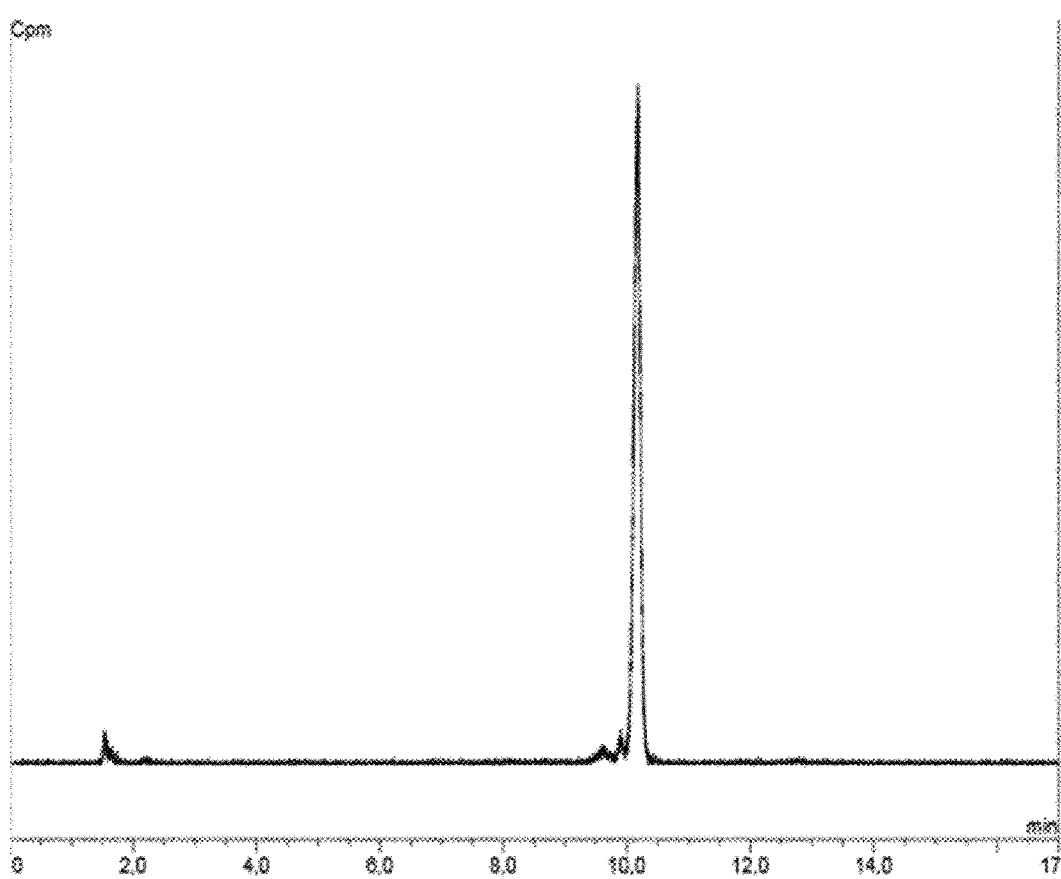

SEQ ID NO: 1 corresponds to the sequence of human CD31.

SEQ ID NO: 2 corresponds to the sequence LAPWKK of a 6 amino acid peptide derived from human or murine CD31.

SEQ ID NO: 3 corresponds to the sequence VRVFLAPWKK of a 10 amino acid peptide derived from murine CD31, also called PepReg CD31.

SEQ ID NO: 4 corresponds to the sequence VRVILAPWKK of a 10 amino acid peptide derived from human CD31.

SEQ ID NO: 5 corresponds to the sequence RVFLAPWK of a 8 amino acid peptide derived from murine CD31, also called P8F.

SEQ ID NO: 6 corresponds to the sequence kwpalfvr of a 8 amino acid peptide, also called P8RI, having the inverted sequence of SEQ ID NO: 5 and consisting of D-amino acids.

SEQ ID NO: 7 corresponds to the sequence RVILAPWK of a 8 amino acid peptide derived from human CD31.

SEQ ID NO: 8 corresponds to the sequence kwpalivr of a 8 amino acid peptide having the inverted sequence of SEQ ID NO: 7 and consisting of D-amino acids.

SEQ ID NO: 9 corresponds to the sequence of murine CD31.

SEQ ID NO: 10 corresponds to the sequence of bovine CD31.

SEQ ID NO: 11 corresponds to the sequence of pig CD31.

SEQ ID NO: 12 corresponds to the amino acids 579 to 601 of sequence SEQ ID NO: 1.

Sequences SEQ ID NO: 13 to 74 are as defined above.

EXAMPLES

Materials and Methods
1. Materials

Reagents were purchased from Sigma-Aldrich Corporation except when otherwise stated and used as received. P8RI (H-kwpalfvr-OH) was synthetized on solid phase with a purity >85% analyzed by RP-HPLC/MS. HYNIC-P8RI was prepared by solid phase peptide synthesis using Fmoc chemistry (yield after RP-HPLC purification 52%, purity by RP-HPLC 96%).

Na$^{99m}$TcO$_4^-$ was obtained from a commercial $^{99}$Mo/$^{99m}$Tc generator (TEKCIS®, Iba molecular, France).

2. Analytical Methods
2.1 HPLC

A Dionex Ultimate 3000 system coupled to a Berthold radiometric detector was used for RP-HPLC analysis. A ACE 3 C18, 3μ, 100 Å, 150×4.6 mm column, at a flow rate of 1 mL/min and with UV detection at 220 nm, was employed with the following mobile phases, A: 0.1% TFA/water), B Acetonitrile (ACN). Gradient was: 0-2 min 23% B, 2-20 min 23-50% B, 20-23 min 50-100% B, 23-25 min 100-23% B, 25-28 min 23% B.

2.2 Thin Layer Chromatography

TLC was performed using a radiochromatogaph (MiniGita, Raytest, Germany). Stationary phase was silica gel (ITLC-SG, Agilent technologies, USA) and different mobile phases were employed. MEK was used to determine the amount of free $^{99m}$TcO$_4^-$ (Rf=1), Anticoagulant Citrate Dextrose Solution (ACD-A, Baxter International, USA) to determine non-peptide-bound $^{99m}$Tc-coligands and $^{99m}$TcO$_4^-$ (Rf=1), 60% ACN for $^{99m}$Tc-colloid (Rf=0).

3. $^{99m}$Tc Radiolabeling
3.1 Tricine as Coligand

In a rubber-sealed N2 purged vial 20 μg of HYNIC-P8RI were incubated with 500 μL of a tricine solution (40 mg/mL in PBS 1× buffer pH 7.2), 80 μL of a tin(II) solution (1 mg/mL in HCl 0.1N), 1 GBq $^{99m}$TcO$_4^-$ eluate and PBS qs a 3 mL total volume for 30 min at room temperature (RT).

3.2 EDDA as Coligand

In a rubber-sealed N2 purged vial 20 μg of HYNIC-P8RI were incubated with 500 μL of a EDDA solution (20 mg/mL in NaOH 0.1 N), 80 μL of a tin(II) solution (1 mg/mL in HCl 0.1N), 1 GBq $^{99m}$TcO$_4^-$ eluate and PBS 1×qs a 3 mL total volume for 30 min at RT.

3.3 Tricine/EDDA Exchange Labeling

Same procedure than tricine as coligand except that 500 μL of a EDDA solution (20 mg/mL in NaOH 0.1N) was added in the reaction vial and heated for 10 min at 100° C.

4. Purification Procedure

Purification was realized using C18 Sep-Pak cartridge (Sep-Pak C18 Plus Light Cartridge, Waters, USA) preactivated with 10 mL of ethanol followed by 10 mL of water and 5 mL of air. After passing the radiolabeling preparation through the cartridge and washing it with 8 mL of water, the radiolabeled peptide was eluted with 80% ACN which was then evaporated under vacuum.

5. In Vitro Stability Study

Stability of $^{99m}$Tc complexes was assessed in fresh human plasma at 37° C. after 0 min, 30 min, 1 hour, 2 hours and 4 hours of incubation at a concentration of 100 μmol/mL. Next, plasma samples were precipitated with methanol and centrifuged (20000 g, 10 min). Supernatants were collected and filtered (Millex-GV 0.22 μm PVDF, Merck Millipore, Germany) then assessed by radio-HPLC.

6. In Vivo Stability Study

74 MBq of 99mTc-HYNIC-P8RI (obtained with tricine/EDDA as coligands) was injected to a male wistar rat. After one hour, rat was sacrificed and urine was directly collected from the bladder using a syringe and analyzed by radio-HPLC after a 0.22 μm filtration (Millex-GV 0.22 μm PVDF, Merck Millipore, Germany).

7. Protein Binding

Protein binding of the purified radiolabeled peptide was determined after 0 min, 30 min, 1 hour, 2 hours and 4 hours of incubation in fresh human plasma at 37° C. and analyzed after size exclusion chromatography (illustra Microspin G-50 Columns, Sephadex G-50, GE Healthcare, UK). G-50 columns were prespun at 2000×g for 1 min then 20 μL of mixture was added and the column was centrifuged at 2000×g for 2 min. Protein binding of the radiolabeled peptide was estimated by measuring columns and eluates in a gamma-counter (Cobra II, Packard Bioscience). In the same time, radiolabeled peptide was incubated for 1 h in PBS 1× at 37° C. as a control.

8. Experimental Models
 8.1. Abdominal Aorta Aneurysm (AAA) Model

Rat model of vascular inflammation that has been set up at the laboratory: the experimental abdominal aorta aneurysm (AAA) induced by local infusion of elastase and followed by intravenous injection of a periodontal bacterium present in human AAA (*Porphyromonas gingivalis*) and known to induce AAA inflammation (Delbosc et al., 2011, PLoS ONE 6(4): e18679. doi:10.1371/journal.pone.0018679).

8.2. Hindlimb Inflammation Model

Rat model of hindlimb inflammation was induced by intramuscular injection of turpentine oil (150 μl) in the right hindlimb, whereas a saline solution (150 μl) was injected in the left hindlimb (contralateral control).

9. SPECT/CT Imaging—AAA Model

Immediately after intravenous injection via the penis vein of 74 MBq of radiolabelled HYNIC-P8RI (obtained using Tricine/EDDA), sequential whole-body acquisitions (every 10 minutes for the first hour) were performed with a hybrid SPECT/CT camera (NanoSPECT/CT, Bioscan Inc.) dedicated to small animals.

10. X Ray CT Scanner, SPECT and SPECT/CT Acquisitions—Right Hindlimb Inflammation Acquisitions were performed 30 min after injection of 80 MBq of 99mTc-HYNIC-P8RI (obtained with tricine/EDDA as coligands) and $^{99m}$Tc-mertiatide, respectively.

Results

1. Radiolabeling

6-Hydrazinopyridine-3-carboxylic acid (HYNIC) was coupled to the N-terminal amino-acid of the P8RI peptide via a 3(PEG) spacer to obtain HYNIC-P8RI.

HYNIC-P8RI was then labeled at high specific activities (>71 GBq/μmol) using tricine, EDDA or Tricine/EDDA as coligands. Labelling yields varied from 65.5% to 98.3% as shown in Table 2. The tricine/EDDA exchange labeling strategy was chosen because of high labeling yield and resulting in a single major specie as analyzed by HPLC (see FIG. 1).

TABLE 2

Labelling yields of 99mTc-HYNIC-P8RI using different coligands

| Co-ligand | N | yield (%) | SD (%) |
|---|---|---|---|
| Tricine | 3 | 98.3 | 0.5 |
| EDDA | 3 | 65.5 | 7.3 |
| Tricine/EDDA | 3 | 93.8 | 2.8 |

2. Stability Study

Figure 2:
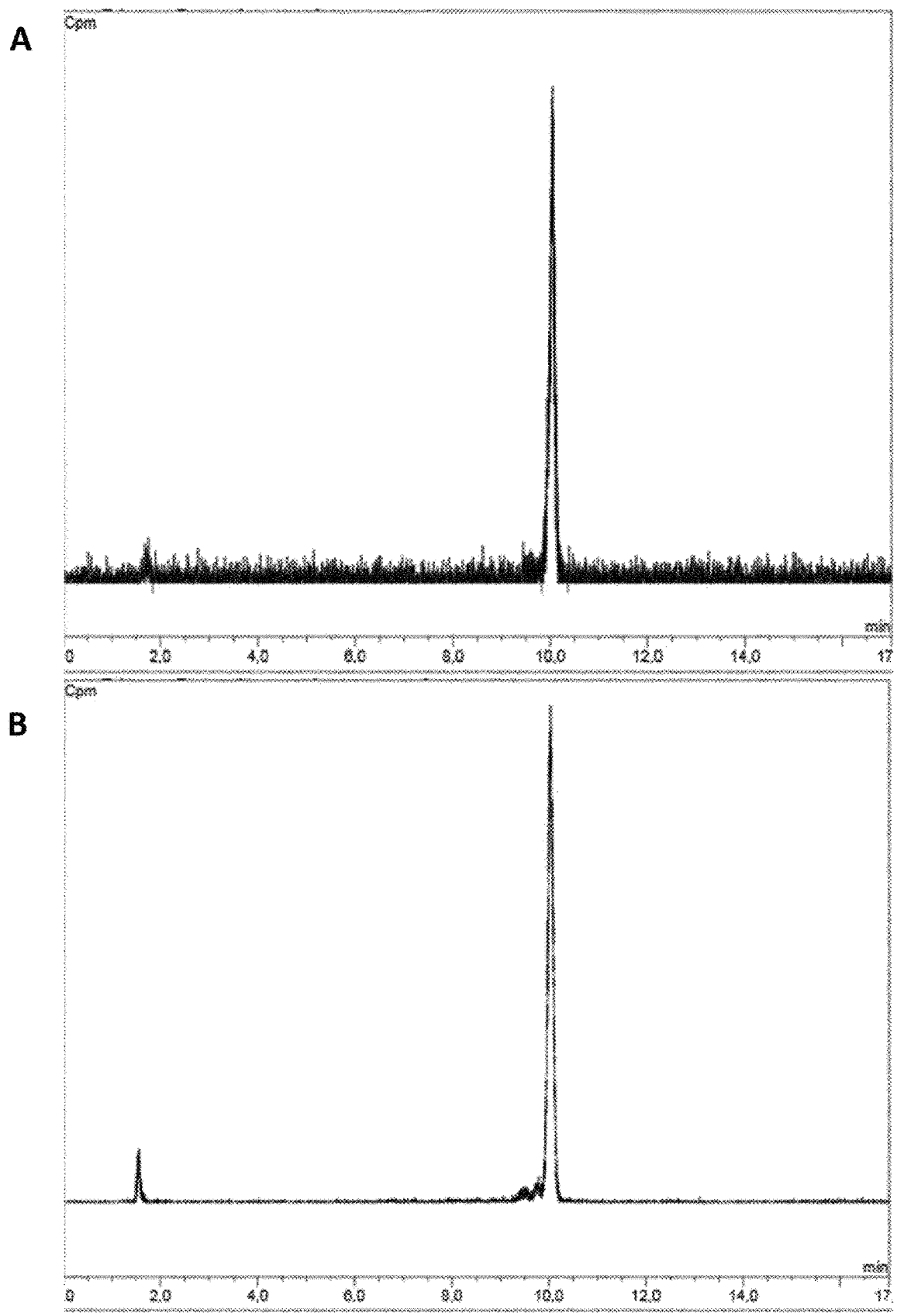
FIG. 2: Radio-HPLC stability study of 99mTc-HYNIC-P8RI with tricine/EDDA as coligands. A: plasma stability after 4 h of incubation in human plasma. B: Radio-HPLC chromatogram of urine collected in a rat bladder 1 hour after injection of 74 MBq of 99mTc-HYNIC-P8RI with tricine/EDDA as coligands. For A and B, peak in the acetonitrile fraction (Tr=10.1 min) corresponds to the initial specie with no signs of degradation.

In vitro stability in human plasma revealed a high stability of the 99mTc complex with no significant release of radiolabeled impurities or radiolabeled peptide degradation. The RCP (radiochemical purity) was superior to 89% after 4 h of incubation (see FIG. 2A). In vivo stability study on rat urine by radio-HPLC analysis showed one major species excreted with a retention time corresponding to the injected radiotracer. This result indicates that 99mTc-HYNIC-P8RI may be excreted unchanged (see FIG. 28).

3. Protein Binding

Very low levels of protein binding as determined by size exclusion chromatography (<5% after 4 h incubation) were found using the Tricine/EDDA coligands exchange labelling strategy. This finding suggests that 99mTc-HYNIC-P8RI may be a hydrophilic compound.

4. SPECT/CT Imaging—AAA Model

Figure 3:
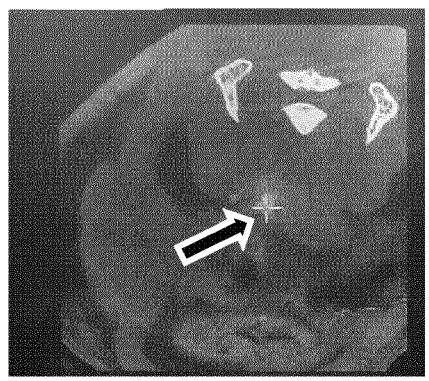
FIG. 3: SPECT/CT images of [99mTc]EDDA/HYNIC-P8RI in a male wistar rat with an abdominal aortic aneurysm (AAA) receiving injection of *Porphyromonas gingivalis* weekly. Images were acquired 30 min after a tracer injection of 74MBq and 21 days after AAA surgery. The axial (A), coronal (B) and sagittal (C) planes of the abdominal region are shown. It is observed the tracer elimination via kidneys (white arrows in B) and the bladder (white arrow in C). Focal uptake of [99mTc]EDDA/HYNIC-P8RI can be observed at the location of the AAA (black arrows in A, B, C).
Figure 3:
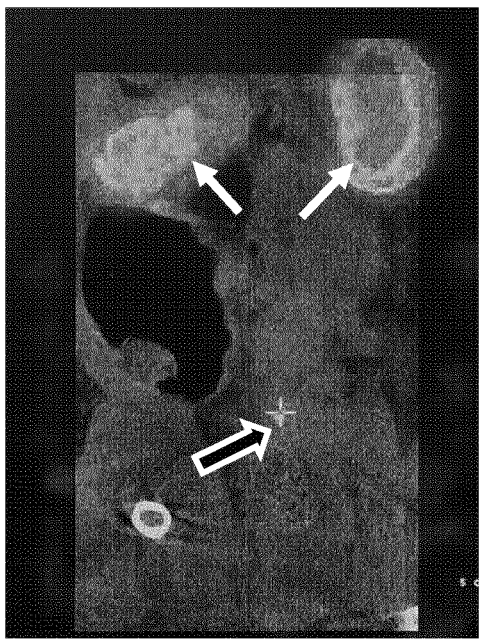
Figure 3:
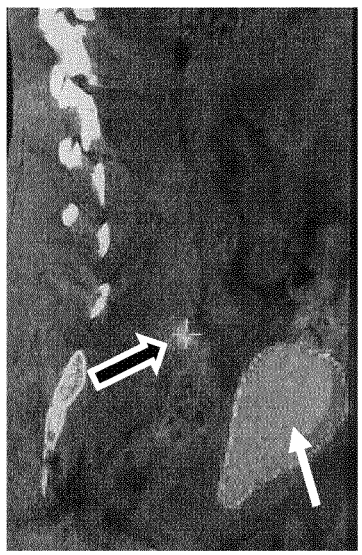

Representative SPECT and CT images were obtained after an acquisition performed 30 min after injection of 99mTc-HYNIC-P8RI (obtained with tricine/EDDA as coligands) in AAA rat as shown in FIG. 3. The pattern of biodistribution indicated almost exclusive renal uptake and excretion. Interestingly, there was a focal uptake of the radiotracer on the aorta pathway corresponding to the location of the AAA.

5. X Ray CT Scanner, SPECT and SPECT/CT Acquisitions—Right Hindlimb Inflammation Model $^{99m}$Tc-HYNIC-P8RI was further assessed in a rat model of right hindlimb inflammation using turpentine oil.

Mertiatide is a non-specific marker of renal function and was used as a negative control, because of its biodistribution pattern close to peptide P8RI (in particular, low molecular weight and quick clearance).

Figure 4:
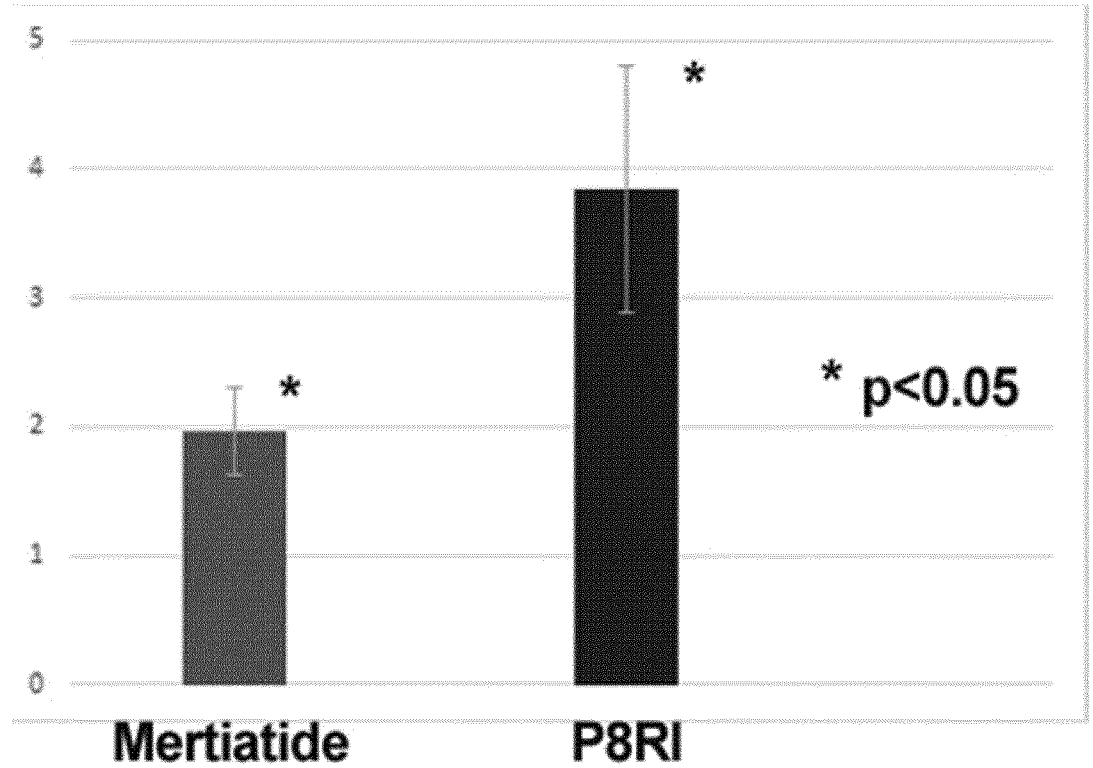
FIG. 4: Comparison of average counts ratio between right hindlimb and left hindlimb measured in the same region of the thigh for technetium-99m radiolabeled mertiatide (n=3) and P8RI injected rats (n=3), in a model of right hindlimb inflammation. Briefly, turpentine oil was injected intramuscularly in Wistar rats right hindlimb and the contralateral thight was injected similarly and simultaneously with saline. SPECT/CT acquisitions were performed 48 hours later and 30 min after injection of 80 MBq of [99mTc]-HYNIC- PEGS-P8RI or [99mTc]-mertiatide. Comparison between the two groups was realized using a Mann-Withney U test, a p value of less than 0.05 was considered significant.

In this model, the technetium-99m radiolabeled P8RI uptake ratio between the turpentine oil injected hindlimb and the saline injected hindlimb was higher compared to the control group injected with technetium-99m radiolabeled mertiatide, thereby confirming the specific binding of P8RI to inflammatory sites (see FIG. 4).

CONCLUSION

The RCP of [99mTc]EDDA/HYNIC-P8RI was >93% (HPLC and ITLC) without any purification and the specific activity was >71 GBq/μmol. There was no significant release of degraded radiolabelled peptide (RCP>89%) and the radiotracer binding to plasma proteins was very low (<5% after 4 h incubation). In vivo, blood clearance of the tracer was almost exclusively renal with a peak activity in kidneys and bladder 1 h after injection, corresponding to the unaltered form of the peptide on HPLC. In addition, $^{99m}$Tc-HYNIC-P8RI uptake by AAA was detectable from 30 min after injection in animals and associated with activated platelets and leukocytes on immunohistochemistry. $^{99m}$Tc-HYNIC-P8RI was also specifically detected in inflammatory sites in a model of right hindlimb inflammation. By specifically targeting activated cells involved in inflammation expressing truncated CD31 ($CD31^{shed}$) and with a rapid blood clearance, radiolabelled P8RI constitutes a useful novel approach in inflammation imaging.

The invention claimed is:

1. A method for imaging inflammatory sites in a subject, said method comprising:
    administering to the subject a labeled $CD31^{shed}$ ligand comprising a $CD31^{shed}$ ligand and at least one imaging label, wherein the $CD31^{shed}$ ligand is a peptide selected from the group consisting of a peptide of sequence SEQ ID NO: 2, a peptide of sequence SEQ ID NO: 3, a peptide of sequence SEQ ID NO: 4, a peptide of sequence SEQ ID NO: 5, a peptide of sequence SEQ ID NO: 6 consisting of D-enantiomer amino acids, a peptide of sequence SEQ ID NO: 7 and a peptide of sequence SEQ ID NO: 8 consisting of D-enantiomer amino acids; and
    detecting the binding of the labeled $CD31^{shed}$ ligand to $CD31^{shed}$ by imaging the subject or at least one body part of the subject,
    thereby imaging inflammatory sites in the subject.

2. The method according to claim 1, wherein said method allows assessing the presence in the subject of an inflammatory condition, or a risk of having an inflammatory condition, and further comprises:
    assessing the presence, localization and/or amount of $CD31^{shed}$ by assessing the detection of the binding of the labeled $CD31^{shed}$ ligand to $CD31^{shed}$ in an image of the subject or of at least one body part of the subject; and
    comparing said presence, localization and/or amount of $CD31^{shed}$ assessed to a control biological image,
thereby determining whether the subject suffers from an inflammatory condition or is at risk of having an inflammatory condition, wherein the inflammatory condition is selected from the group consisting of rheumatoid arthritis, multiple sclerosis, allergies, myopathy, inflammatory bowel disease, psoriasis, atopic dermatitis, cerebral amyloid angiopathy, vasculitis, systemic lupus erythematosus, Graves' disease, diabetes mellitus, acute or chronic grant rejection, cancer, thrombosis, atherothrombosis, and neurodegenerative disease.

3. The method according to claim 1, wherein said method allows assessing the risk of recurrence of an inflammatory condition in a subject suffering from an inflammatory condition, and comprises:
    administering an anti-inflammatory treatment to the subject;
    carrying out the steps of the method according to claim 1 at least two times, first at the end of said anti-inflammatory treatment and then after said anti-inflammatory treatment; and
    comparing the images obtained at the end of the anti-inflammatory treatment and after the anti-inflammatory treatment,
    thereby determining the risk of recurrence of an inflammatory condition,
    wherein the inflammatory condition is selected from the group consisting of rheumatoid arthritis, multiple sclerosis, allergies, myopathy, inflammatory bowel disease, psoriasis, atopic dermatitis, cerebral amyloid angiopathy, vasculitis, systemic lupus erythematosus, Graves' disease, diabetes mellitus, acute or chronic grant rejection, cancer, thrombosis, atherothrombosis, and neurodegenerative disease.

4. The method according to claim 1, wherein said method allows monitoring efficacy of an anti-inflammatory treatment administered to a subject suffering from an inflammatory condition, and comprises:
    carrying out the steps of the method according to claim 1;
    administering an anti-inflammatory treatment to the subject;
    repeating the steps of the method according to claim at least once during administration of the treatment; and
    comparing the images obtained before administration of the anti-inflammatory treatment and during administration of the anti-inflammatory treatment,
    thereby monitoring efficacy of the anti-inflammatory treatment,
    wherein the inflammatory condition is selected from the group consisting of rheumatoid arthritis, multiple sclerosis, allergies, myopathy, inflammatory bowel disease, psoriasis, atopic dermatitis, cerebral amyloid angiopathy, vasculitis, systemic lupus erythematosus, Graves' disease, diabetes mellitus, acute or chronic grant rejection, cancer, thrombosis, atherothrombosis, and neurodegenerative disease.

5. The method according to claim 1, wherein said CD31shed ligand is a peptide of sequence SEQ ID NO: 5, a peptide of sequence SEQ ID NO: 6 consisting of D-enantiomer amino acids, a peptide of sequence SEQ ID NO: 7, or a peptide of sequence SEQ ID NO: 8 consisting of D-enantiomer amino acids.

6. The method according to claim 1, wherein said imaging label is a radionuclide.

7. The method according to claim 1, wherein said imaging label is a radionuclide detectable by Positron Emission Tomography (PET), Single Photon Emission Computed Tomography (SPECT), a hybrid of SPECT and/or PET or their combinations.

8. The method according to claim 1, wherein said imaging label is a radionuclide selected from the group consisting of technetium-99m (99mTc), gallium-67 (67Ga), gallium-68 (68Ga) yttrium-90 (90Y), indium-111 (111In), rhenium-186 (186Re), fluorine-18 (18F), copper-64 (64Cu), and thallium-201 (201T1).

9. The method according to claim 1, wherein said $CD31^{shed}$ ligand is a peptide of sequence SEQ ID NO: 6 consisting of D-enantiomer amino acids, or a peptide of sequence SEQ ID NO: 8 consisting of D-enantiomer amino acids, and wherein said imaging label is a radionuclide being 99mTc.

10. The method according to claim 1, wherein said $CD31^{shed}$ ligand comprises 6-hydrazinopyridine-3-carboxylic acid (HYNIC).

11. An in vitro method for detecting $CD31^{shed}$ in a biological sample of a subject, said biological sample comprising cells, wherein said method comprises:

contacting the biological sample of the subject with a labeled $CD31^{shed}$ ligand comprising a $CD31^{shed}$ ligand and at least one imaging label, wherein said $CD31^{shed}$ ligand is a peptide selected in the group consisting of a peptide of sequence SEQ ID NO: 2, a peptide of sequence SEQ ID NO: 3, a peptide of sequence SEQ ID NO: 4, a peptide of sequence SEQ ID NO: 5, a peptide of sequence SEQ ID NO: 6 consisting of D-enantiomer amino acids, a peptide of sequence SEQ ID NO: 7 and a peptide of sequence SEQ ID NO: 8 consisting of D-enantiomer amino acids; and imaging the labeled $CD31^{shed}$ ligand bound to $CD31^{shed}$, thereby detecting the presence of $CD31^{shed}$ on the surface of the cells comprised within the biological sample of the subject.

12. The method according to claim 11, wherein said $CD31^{shed}$ ligand is a peptide of sequence SEQ ID NO: 6 consisting of D-enantiomer amino acids, or a peptide of sequence SEQ ID NO: 8 consisting of D-enantiomer amino acids, and wherein said imaging label is a radionuclide being 99mTc.

* * * * *